(12) United States Patent
Verseput

(10) Patent No.: US 8,219,328 B2
(45) Date of Patent: **\*Jul. 10, 2012**

(54) SYSTEM AND METHOD FOR AUTOMATING SCIENTIFIC AND ENGINEERING EXPERIMENTATION FOR DERIVING SURROGATE RESPONSE DATA

(75) Inventor: Richard P. Verseput, McKinleyville, CA (US)

(73) Assignee: S-Matrix, Eureka, CA (US)

( * ) Notice: Subject to any disclaimer, the term of this patent is extended or adjusted under 35 U.S.C. 154(b) by 50 days.

This patent is subject to a terminal disclaimer.

(21) Appl. No.: 12/758,769

(22) Filed: Apr. 12, 2010

(65) Prior Publication Data

US 2010/0250147 A1 Sep. 30, 2010

Related U.S. Application Data

(63) Continuation-in-part of application No. 12/463,311, filed on May 8, 2009, and a continuation-in-part of application No. 11/750,961, filed on May 18, 2007, now Pat. No. 7,613,574.

(60) Provisional application No. 61/168,384, filed on Apr. 10, 2009.

(51) Int. Cl.
*G06F 15/16* (2006.01)
(52) U.S. Cl. .......... 702/32; 702/19; 435/325; 435/6; 435/91.2; 707/1; 709/217; 709/204
(58) Field of Classification Search ............ 702/19, 702/32; 435/325, 6, 91.2; 436/86; 707/1; 700/100; 709/217, 204
See application file for complete search history.

(56) References Cited

U.S. PATENT DOCUMENTS

| 4,412,288 | A | * | 10/1983 | Herman .................... 600/342 |
|---|---|---|---|---|
| 5,369,566 | A | | 11/1994 | Pfost et al. |
| 5,419,328 | A | | 5/1995 | Goh et al. |
| 5,959,297 | A | | 9/1999 | Weinberg et al. |
| 6,004,617 | A | | 12/1999 | Schultz et al. |
| 6,030,917 | A | | 2/2000 | Weinberg et al. |
| 6,034,775 | A | | 3/2000 | McFarland et al. |
| 6,178,382 | B1 | | 1/2001 | Roederer et al. |
| 6,489,168 | B1 | | 12/2002 | Wang et al. |

(Continued)

FOREIGN PATENT DOCUMENTS

WO WO 00/52646 9/2000
(Continued)

OTHER PUBLICATIONS

Winton, Don. "Process Capability Studies", 1999, 16 pages.
(Continued)

*Primary Examiner* — Carol Tsai
(74) *Attorney, Agent, or Firm* — Sawyer Law Group, P.C.

(57) ABSTRACT

The present invention provides a system and method for automatically deriving unique surrogate response data from experiment results in which inherent data loss occurs in a sufficient number of the samples to disallow quantitative effects estimation at the experimenter's desired level of confidence for statistical significance. In part, the unique surrogate response data sets of the present invention have one or more of four primary characteristics including: each is numerically analyzable; each may be readily or directly obtained when inherent data loss occurs; each provides a response value for an experiment trial; and each provides information on the effect of a change made to the process or system that would have been obtainable if the experiment samples had had no inherent data loss.

18 Claims, 22 Drawing Sheets

U.S. PATENT DOCUMENTS

| | | | |
|---|---|---|---|
| 6,581,012 B1 | 6/2003 | Aryev et al. | |
| 6,658,429 B2 | 12/2003 | Dorsett, Jr. | |
| 6,728,641 B1 * | 4/2004 | Cawse | 506/11 |
| 6,754,543 B1 | 6/2004 | Wold | |
| 6,853,923 B2 | 2/2005 | Trygg et al. | |
| 6,909,974 B2 | 6/2005 | Yung et al. | |
| 6,947,953 B2 | 9/2005 | Herzenberg et al. | |
| 6,996,550 B2 | 2/2006 | Wang et al. | |
| 7,194,374 B2 | 3/2007 | Kobayashi et al. | |
| 7,213,034 B2 | 5/2007 | Dorsett, Jr. | |
| 7,427,479 B2 | 9/2008 | Karger et al. | |
| 7,474,925 B2 | 1/2009 | Renner | |
| 7,519,605 B2 | 4/2009 | Vailaya et al. | |
| 2001/0039539 A1 * | 11/2001 | Sartiel et al. | 707/1 |
| 2002/0049782 A1 | 4/2002 | Herzenberg et al. | |
| 2002/0152057 A1 | 10/2002 | Wang et al. | |
| 2002/0156792 A1 | 10/2002 | Gombocz et al. | |
| 2003/0004612 A1 | 1/2003 | Domanico et al. | |
| 2003/0050763 A1 | 3/2003 | Arrit et al. | |
| 2003/0149501 A1 | 8/2003 | Tuszynski | |
| 2003/0200004 A1 | 10/2003 | Renner | |
| 2004/0034478 A1 | 2/2004 | Yung et al. | |
| 2004/0148291 A1 | 7/2004 | Dorsett, Jr. | |
| 2005/0026131 A1 * | 2/2005 | Elzinga et al. | 434/365 |
| 2005/0044110 A1 | 2/2005 | Herzenberg et al. | |
| 2005/0080588 A1 | 4/2005 | Kobayashi et al. | |
| 2005/0154701 A1 | 7/2005 | Parunak et al. | |
| 2005/0273475 A1 | 12/2005 | Herzenberg et al. | |
| 2005/0278321 A1 | 12/2005 | Vailaya et al. | |
| 2006/0003351 A1 * | 1/2006 | Karger et al. | 435/6 |
| 2006/0074726 A1 | 4/2006 | Forbes et al. | |
| 2007/0048863 A1 * | 3/2007 | Rodgers et al. | 435/325 |
| 2008/0137080 A1 * | 6/2008 | Bodzin et al. | 356/300 |
| 2008/0215705 A1 * | 9/2008 | Liu et al. | 709/217 |

FOREIGN PATENT DOCUMENTS

| | | |
|---|---|---|
| WO | 2004038602 | 5/2004 |

OTHER PUBLICATIONS

Shabir, Ghulam. "Validation of high-performance liquid chromatography methods for pharmaceutical analysis", 2003, Journal of Chromatography, vol. 987, pp. 57-66.

"Var Tran 3.2 Tutorials: Guide to Getting Started", 2005, 32 pages.

Sematech, "Sematech qualification plan guidelines for engineering", 1995, 106 pages.

Lukulay et al., "Automating HPLC and GC Analytical Method Validation", Data and Review, May 2, 2005, 5 pgs.

Kwangsun Yoon, "The Propagation of Errors in Multiple-attribute Decision Analysis: A Practical Approach", The Journal of the Operational Research Society, vol. 40, No. 7 (Jul. 1989), pp. 681-686.

* cited by examiner

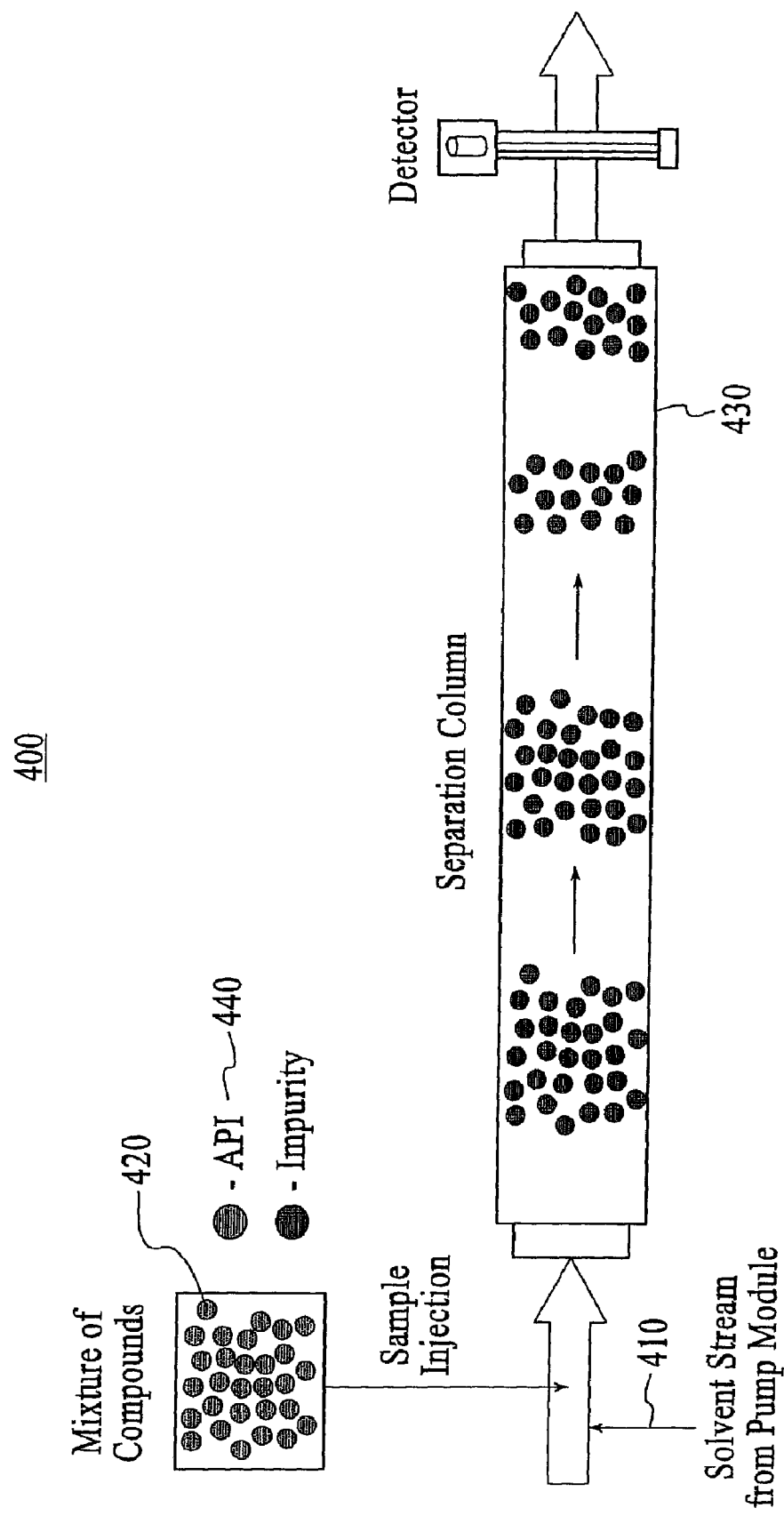
FIG.4A  HPLC System as a Process

HPLC Hardware Framework

Automated experiment construction and file-less export to ICP as ready-to-run in the ICP's native data and file formats.

Results Data Sets in ICP

Import from ICP

- Data Analysis
- 2D, 3D, 4D (Trellis) Graphing
- Numerical & Graphical Optimization
- Formal Reporting
  HTML, PDF, DOC, RTF, TXT Automated experiment running and file-less import from ICP as completed results data sets

| TRIAL NO. | STUDY FACTORS ||||| EXPERIMENT RESULTS ||||
|---|---|---|---|---|---|---|---|---|---|
| | INITIAL HOLD TIME | GRADIENT TIME | FINAL % ORGANIC | COLUMN TYPE | 3. RESOLUTION | 4. RESOLUTION | 4A. RESOLUTION | 5. RESOLUTION |
| 1 | 1 | 20 | 50 | A | 2.94 | | 1.18 | 16.54 |
| 2 | 1 | 20 | 65 | B | 1.17 | | 2.54 | 2.53 |
| 3 | 1 | 25 | 50 | A | 2.94 | | 1.13 | 1.66 | 3.42 |
| 4 | 4 | 15 | 80 | B | 1.27 | | 3.24 | 2.12 |
| 5 | 1 | 15 | 80 | A | 2.48 | | 1.04 | | 4.09 |
| ... | ... | ... | ... | ... | ... | ... | ... | ... |
| 11 | 1 | 15 | 65 | A | 2.44 | | 1.13 | | 4.36 |
| 12 | 1 | 25 | 80 | B | 1.21 | | 3.28 | 2.2 | 4.86 |
| 13 | 4 | 15 | 80 | B | 1.39 | | 4.9 | 2.64 | 5.08 |
| 14 | 2.5 | 25 | 65 | B | 0.69 | | 3.52 | 1.19 | 5.1 |
| 15 | 4 | 25 | 80 | B | 1.23 | | 3.27 | 2.12 | 4.68 |
| ... | ... | ... | ... | ... | ... | ... | ... | ... |
| 40 | 1.75 | 22.5 | 72 | A | | | 1.58 | | 4.32 |
| 41 | 1 | 15 | 80 | B | | | 3.21 | 3.98 | 5.06 |
| 42 | 3.25 | 22.5 | 72 | A | | | 1.33 | | 3.98 |
| 43 | 2.5 | 20 | 80 | B | | 0.8 | 3.6 | 1.1 | 5.25 |
| 44 | 4 | 15 | 50 | A | | | 1.31 | | 4.71 |
| 45 | 2.5 | 25 | 50 | A | | | 1.42 | | 3.99 |
| 46 | 1 | 20 | 50 | B | | 0 | 3.62 | 2.56 | 5.42 |
| 47 | 1 | 15 | 50 | B | | | 3.16 | 3.9 | 3.99 |
| 48 | 4 | 15 | 50 | B | | | 3.01 | 4.76 | 3.78 |
| 49 | 4 | 25 | 65 | A | | | 1.44 | | 4.62 |
| 50 | 4 | 15 | 80 | A | | 0 | 2.5 | | 4.49 |

FIG. 13

| REGRESSION STATISTIC NAME | STATISTIC VALUE |
|---|---|
| R SQUARE | 0.0986 |
| ADJ. R SQUARE | 0.0639 |

FIG. 14

|  | STUDY FACTORS | | | EXPERIMENT RESULTS | |
|---|---|---|---|---|---|
| TRIAL NO. | INITIAL HOLD TIME | GRADIENT TIME | FINAL % ORGANIC | COLUMN TYPE | TOTAL PEAKS | RESOLVED PEAKS (>1.50) |
| 1 | 1 | 20 | 50 | A | 11 | 7 |
| 2 | 1 | 20 | 65 | B | 21 | 16 |
| 3 | 1 | 25 | 50 | A | 15 | 11 |
| 4 | 4 | 15 | 80 | B | 12 | 9 |
| 5 | 1 | 15 | 80 | A | 15 | 9 |
| ... | ... | ... | ... | ... | ... | ... |
| 11 | 1 | 15 | 65 | A | 12 | 9 |
| 12 | 1 | 25 | 80 | B | 12 | 9 |
| 13 | 4 | 15 | 80 | B | 12 | 8 |
| 14 | 2.5 | 25 | 65 | B | 13 | 9 |
| 15 | 4 | 25 | 80 | B | 11 | 8 |
| ... | ... | ... | ... | ... | ... | ... |
| 40 | 1.75 | 22.5 | 72 | A | 13 | 9 |
| 41 | 1 | 15 | 80 | B | 13 | 9 |
| 42 | 3.25 | 22.5 | 72 | A | 13 | 9 |
| 43 | 2.5 | 20 | 80 | B | 14 | 9 |
| 44 | 4 | 15 | 50 | A | 10 | 7 |
| 45 | 2.5 | 25 | 50 | A | 11 | 6 |
| 46 | 1 | 20 | 50 | B | 13 | 10 |
| 47 | 1 | 15 | 50 | B | 11 | 9 |
| 48 | 4 | 15 | 50 | B | 11 | 9 |
| 49 | 4 | 25 | 65 | A | 15 | 10 |
| 50 | 4 | 15 | 80 | A | 12 | 9 |

FIG. 15

| PARAMETER NAME | COEFFICIENT VALUE | COEFFICIENT STANDARD ERROR | COEFFICIENT t STATISTIC | P-VALUE | F-RATIO | LOWER 95% CONFIDENCE LIMIT | UPPER 95% CONFIDENCE LIMIT |
|---|---|---|---|---|---|---|---|
| CONSTANT | 12.33 | 0.23 | ... | ... | ... | 11.87 | 12.79 |
| COLUMN B | 1.82 | 0.41 | 4.4382 | 0.0001 | 19.6975 | 0.99 | 2.64 |
| (GRAD. $\Delta t$)*% ORGANIC | -0.54 | 0.23 | -2.3442 | 0.0239 | 5.4955 | -1.00 | -0.08 |
| % ORGANIC*COL. B | 0.75 | 0.31 | 2.3918 | 0.0213 | 5.7207 | 0.12 | 1.38 |
| (% ORGANIC)$^2$*COL. B | -1.13 | 0.50 | -2.2585 | 0.0292 | 5.1010 | -2.13 | -0.12 |
| (INITIAL $\Delta t$)$^2$*GRAD. $\Delta t$ | 0.56 | 0.23 | 2.4658 | 0.0178 | 6.0803 | 0.10 | 1.02 |

FIG. 16

| PARAMETER NAME | COEFFICIENT VALUE | COEFFICIENT STANDARD ERROR | COEFFICIENT t STATISTIC | P-VALUE | F-RATIO | LOWER 95% CONFIDENCE LIMIT | UPPER 95% CONFIDENCE LIMIT |
|---|---|---|---|---|---|---|---|
| CONSTANT | 9.08 | 0.10 | ... | ... | ... | 8.87 | 9.29 |
| % ORGANIC | -0.33 | 0.14 | -2.3433 | 0.0240 | 5.4911 | -0.61 | -0.05 |
| % ORGANIC*COL. B | 0.96 | 0.22 | 4.4181 | 0.0001 | 19.5195 | 0.52 | 1.40 |
| (% ORGANIC)$^2$*COL. B | -1.23 | 0.26 | -4.7122 | <+/- 0.0001 | 22.2052 | -1.76 | -0.70 |
| (INITIAL $\Delta t$)$^2$*GRAD. $\Delta t$ | 0.24 | 0.12 | 2.0247 | 0.0494 | 4.0994 | 0.0006 | 0.48 |
| (INITIAL $\Delta t$)$^2$*COL. $\Delta f$ | 0.59 | 0.24 | 2.4960 | 0.0167 | 6.2302 | 0.11 | 1.07 |

FIG. 17

SYSTEM AND METHOD FOR AUTOMATING SCIENTIFIC AND ENGINEERING EXPERIMENTATION FOR DERIVING SURROGATE RESPONSE DATA

CROSS-REFERENCE TO RELATED APPLICATIONS

This application is a Continuation-In-Part of U.S. Pat. No. 7,613,574, issued Nov. 3, 2009, entitled "SYSTEM AND METHOD FOR AUTOMATING SCIENTIFIC AND ENGINEERING EXPERIMENTATION FOR DERIVING SURROGATE RESPONSE DATA," a Continuation-In-Part of U.S. application Ser. No. 12/463,311, filed May 8, 2009, entitled, "SYSTEM AND METHOD FOR AUTOMATING SCIENTIFIC AND ENGINEERING EXPERIMENTATION FOR DERIVING SURROGATE RESPONSE DATA," and claims the benefit of priority of U.S. Patent Application No. 61/168,384, filed Apr. 10, 2009, entitled "SYSTEM AND METHOD FOR AUTOMATING SCIENTIFIC AND ENGINEERING EXPERIMENTATION FOR DERIVING SURROGATE RESPONSE DATA," all of which are incorporated herein by reference.

FIELD OF THE INVENTION

The present invention relates generally to automating research, development, and engineering experimentation processes and work and more specifically to providing a system and method for automated experimentation and automatically deriving unique surrogate response data from experiment results.

BACKGROUND OF THE INVENTION

The execution steps in most research, development, and engineering experiments generally involve manual operations carried out on unconnected technology platforms. The scientist or engineer works in what are essentially isolated technology islands with manual operations providing the only bridges. To illustrate, when there is a Standard Operating Practice (SOP) Guide for the experimental work, it is often an electronic document, for example in Microsoft Word. The experimental plan (Step 1) within the SOP Guide has to be transferred to the target device (instrument, instrument platform, or component module for execution (Step 2) by manually re-keying the experiment into the device's instrument control program (ICP)—the device's controlling application software. In a few cases the statistical analysis of results (Step 3a) can be done within the ICP, but it is most often done within a separate statistical analysis software package or spreadsheet program such as Microsoft Excel. This also requires manually transferring the results data from the ICP to the analysis software package. Reporting of results (Step 3b) is usually carried out in Microsoft Word, and therefore requires the manual transfer of all results tables and graphs from the separate statistical analysis software package. The manual operations within the general execution sequence steps are presented below. The isolated technology islands are illustrated in FIGS. 1 and 2.

FIG. 1 illustrates the manual tools and operations involved in carrying out a research and development experiment. In this work a statistical experiment design protocol is first generated, via step 12. This protocol is developed manually and off-line using non-validated tools such as Microsoft Word. The protocol then must be approved, once again manually and off-line, via step 14. When required, sample amounts are then calculated using non-validated tools such as Microsoft Excel, via step 16. Thereafter the samples are prepared, via step 18 and the experiment is run on a target device, via step 20, for example, a high-performance liquid chromatograph (HPLC). Running the experiment requires manually re-constructing the statistical design within the target device's ICP. When this software does not exist, or does not allow for full instrument control, the experiment must be carried out in a fully manual mode by manually adjusting instrument settings between experiment runs.

FIG. 2 illustrates the manual tools and operations involved in analyzing the data and reporting the results of the research and development experiment, via step 22. The analysis and reporting of data is accomplished by first statistically analyzing and interpreting the experiment data, off-line, using non-validated tools such as Microsoft Excel. Next, it is determined whether or not there is a need for more experiments, possibly using off-line generic Design of Experiments (DOE) software, via step 24. Then, data are entered and a report is written, via step 26. Finally, the report is archived, via step 28. As is seen from the above, the research, development, and engineering experimentation process involves a series of activities that are currently conducted in separate "technology islands" that require manual data exchanges among the tools that are used for each activity. However, until now, no overarching automation technology exists that brings together all the individual activities under a single integrated-technology platform that is adapted to multiple devices and data systems.

Method development activities encompass the planning and experimental work involved in developing and optimizing an analytical method for its intended use. These activities are often captured in company Standard Operating Procedure (SOP) documents that may incorporate Food and Drug Administration (FDA) and International Conference on Harmonization (ICH) requirements and guidances. Method development SOP documents include a description of all aspects of the method development work for each experiment type (e.g. early phase analytical column screening, late phase method optimization, method robustness) within a framework of three general execution sequence steps: (1) experimental plan, (2) instrumental procedures, and (3) analysis and reporting of results. The individual elements within these three general steps are presented below.

Step 1: Generate Experimental Plan
    Select experiment type
    Select target instrument
    Define study variables:
        analyte concentrations
        instrument parameters
        environmental parameters
    Specify number of levels per variable
    Specify number of preparation replicates per sample
    Specify number of injections per preparation replicate
    Integrate standards
    Include system suitability injections
    Define Acceptance Criteria
Step 2: Construct Instrumental Procedures
    Define required transformations of the experiment plan into the native file or data formats of the instrument's controlling ICP software (construction of Sample Sets and Method Sets or Sequence and Method files).
    Specify number of injections (rows)
    Specify type of each injection (e.g., sample, standard)
Step 3: Analyze Data and Report Results
    Specify analysis calculations and report content and format
    Carry out numerical analyses Compare analysis results to acceptance criteria (FDA & ICH requirements)

Specify graphs and plots that should accompany the analysis

Construct graphs and plots

Compile final report

The execution steps in analytical method development generally involve manual operations carried out on unconnected technology platforms. To illustrate, an SOP Guide for the development of an HPLC analytical method is often an electronic document in Microsoft Word. The experimental plan (Step 1) within the SOP Guide has to be transferred to the HPLC instrument for execution (Step 2) by manually re-keying the experiment into the instrument platform's ICP—in the case of an HPLC this is typically referred to as a chromatography data system (CDS). In a few cases the statistical analysis of results (Step 3) can be performed within the CDS, but it is most often carried out within a separate statistical analysis software package or spreadsheet program such as Microsoft Excel. This also requires manually transferring the results data from the CDS to the analysis software package. Reporting of results (Step 3) is usually carried out in Microsoft Word, and therefore requires the manual transfer of all results tables and graphs from the separate statistical analysis software package. The manual operations within the three general execution sequence steps are presented below.

Step 1—Experimental Plan

Development plan developed in Microsoft Word.

Experimental design protocol developed in off-line DOE software.

Step 2—Instrumental Procedures

Manually build the Sequences or Sample Sets and instrument methods in the CDS.

Raw peak (x, y) data reduction calculations performed by the CDS (e.g. peak area, resolution, retention time, concentration).

Step 3a—Statistical Analysis

Calculated results manually transferred from the CDS to Microsoft Excel.

Statistical analysis usually carried out manually in Microsoft Excel.

Some graphs generated manually in Microsoft Excel, some obtained from the CDS.

Step 3b—Reporting of Results

Reports manually constructed from template documents in Microsoft Word.

Graphs and plots manually integrated into report document.

It is realized that prior art systems in the area do not address the overarching problem of removing the manually intensive steps required to bridge the separate technology islands. Similarly, it is also realized from the prior art that inherent data loss is known to occur in sampling of experimental results to impact quantitative effect estimations and thereby degrade and typically render inaccurate statistical confidences from experimental results. However, the prior art is not instructive in assisting in overcoming these problems to improve the accuracy or analyzability of experimental results and sampling, nor is the prior art instructing in overcoming deficiencies enabling one to develop a readily obtainable solution to overcome inherent data loss, provide an identifiable metric for separate experimental undertakings, or provide information about resulting effects where experimental samples contain inherent data losses.

For instance, often trial runs of research and development (R&D) experiments may be carried out by making changes to one or more controllable parameters (as used herein such may include but not be limited to study factors, instrument settings, controllable parameters of instrumentation, a set of discrete process events, or other experimentation factors with other factors remaining constant (as used herein the controlled portion of an experiment or experimental run or trial) of a process or system and then measuring test samples obtained from in-process sampling or process output. Typically, an objective of a researcher in these undertakings is to identify and quantify the effects of the parameter changes on the identified important process output quality attributes or performance characteristics that are being measured. The quantified effects can then be used to define the parameter settings that will give the desired process output results.

FIG. 3 illustrates a generalized flow diagram of a process in a predetermined process flow direction (305) consisting of four discrete elements (300): base material input (310), key reactant input (320), heating (330), and chemical reaction (340). For the avoidance of doubt, FIG. 3 and its related embodiments are foundational to the present invention herein. The flow diagram 300 also contains an in-process measurement step at 335 and a process endpoint measurement step at 350. In this generalized process 300 the base material element may have one or more controllable parameters such as material feed rate or be of two or more blended components including base material formulation for example. In addition, the measurements of the quality attributes or performance characteristics of interest may actually be taken within the process stream, as would be done by an in-process measurement system, or on the process output material.

The process 300 of FIG. 3 can similarly be analogized via a chemical separation process performed by instrumentation such as that of an HPLC. FIG. 4A is demonstrative of such an adaptation of the general process flow diagram 300 of FIG. 3 to that of an HPLC. In FIG. 4A, the flow diagram 400 comprises three primary HPLC process elements: solvent delivery (410), sample injection (420), and a separation chamber (430).

In FIG. 4A, method development experiments may be performed on controllable parameters within the HPLC to identify the parameter settings that are optimum for the separation of a given mixture of compounds. In such experiments, one critical performance characteristic being measured, for example, may be the degree of separation of the mixture into isolated pure individual compounds, as is further defined by the legend at 440. However, and more particularly in typical practical applications such as those within the pharmaceutical industry, the active pharmaceutical ingredient (API) and one or more degradants and/or impurities in a drug product often represents a normal mixture of compounds for which an HPLC method must be developed. As is known from practical applications under tradition methods, accurately measuring the amount of API in a test sample (or actual sample) with an HPLC would require that the instrument first separate the API from the degradants and/or impurities.

As used herein, the term "impurities" are defined to include but not be limited to components of the drug product formulation, which may also be termed excipients, or contaminants that come from various points or stages in the process or even the product packaging of an affected product or sample. For example, an impurity may be a plastic compound from a product container that may contaminate the surface of the drug tablet for instance. By further example, a test sample may be a dissolved tablet (i.e., the solid dosage form of the drug product) that contains the API and impurities. As used herein, the term "degradants" are defined as breakdown products of a sample API or impurity, i.e., molecules which result from the decomposition of the API or impurity. As an additional further example, a test sample may be a dissolved tablet (i.e., the solid dosage form of the drug product) that is subject to stress conditions which attempt to force the degradation of the API and impurity compounds in the sample.

Therefore a critical HPLC method development experiment objective in a traditional practice application may include identifying the instrument operating conditions that separate the API from any degradants and impurities in a test mixture to the degree required (i.e., accuracy level) to accurately measure the API amount. Further in separation method development experiments, for example, some of the HPLC parameter settings used in the experiment trials can result in the inability to accurately measure a critical performance characteristic, such as compound separation. These issues are known to be a significant challenge for researchers and commercial entities alike.

The consequences of these limitations realized by many in the field then are the inherent data losses in one or more experiment trials which can then result in the inability to quantitatively analyze the experiment results and draw any meaningful conclusions.

FIG. 4B depicts an instrument hardware framework 450 associated with an HPLC instrument system. The HPLC framework 450 comprises several process elements with controllable parameters that can be experimentally addressed. The process elements include: solvent formulation and solvent pH adjusted using a controllable valve module for solvent selection (CVM—Solvent Switching) (451), the solvent flow rate (Pump Module) (452), the type of separation column adjusted using a controllable valve module for column switching (CVM—Column Switching) (453), a sampler (454) and a detector (455).

For FIG. 4B, a typical experiment (i.e., method development experiment) may be comprised of conducting one or more trials where a trial consists of operating the HPLC instrument at one or more predetermined settings of the study parameters, injecting a small amount of the sample mixture into the solvent stream and measuring critical performance characteristics such as the degree of separation of the individual sample compounds at the endpoint of the process 455.

By exemplar, objectives of experimentation under the framework of FIG. 4B in view of the process set forth in FIG. 4A, may include attempting to separate out one or more APIs from impurities or degradants. In such experiments, for example, the controllable parameters of the CVM modules (451 and 453) and the Pump Module (452) may be selected for experimental study. In such experiments, CVM solvent switching parameters may be adjusted between experiment trials to deliver a solvent mix at a different pH and the results captured. In such experiments, CVM column switching parameters may also be adjusted so as to employ a different column, for example, in each experimental trial undertaken. Similarly, in such experiments, pump module parameters may be adjusted between trials to both change the rate at which the solvent formulation is changed (i.e., proportion of organic solvent increased) during a trial run and to deliver the solvent formulation at a different flow rate. However, as will become further evident, in these types of experiments, despite the objectives of experimentation including attempts to separate out one or more APIs from impurities and/or degradants by selecting predetermined controllable parameters for experimental study, the results can be inaccurate.

FIG. 4C depicts a graphical chromatogram representation 460 of experimental results data obtained from a particular trial run trial in one of the experimental runs under assessment herein (e.g. trial run 11), wherein the "raw" results depicted in the figure are in the form of "absorbance peaks." A peak typically occurs when a compound absorbs light transmitted through the solvent stream and is detected by the detector as the compound passes the detector at a given time X, wherein the baseline condition represents zero absorbance of the light.

As used herein, an "absorbance peak" or "peak" generally means a vertical spike (Y axis deviation) along a horizontal line in the graph from baseline conditions (where Y=zero) occurring at a given X axis time interval. As also used herein, a compound's "retention time" is defined as the time from injection to detection, and, in the chromatogram, this time is the X-axis value corresponding to the peak's maximum Y value.

In FIG. 4C, poorly separated peaks are apparent at 461 and 462. Interpretatively, each peak in FIG. 4C corresponds to at least one compound (i.e., the API or an impurity). It should also be readily recognized that the area under a given peak is proportional to the amount of absorbed light, which is in turn proportional to the amount of the corresponding compound in the solvent stream passing the detector at the time indicated on the X axis in the chromatogram.

However, problematically, translating the measured area of a given peak into an amount of the corresponding compound is typically accurate only where the peak in a chromatogram is the result of only one compound. As a result, accurately measuring the amount of an individual compound in a sample using traditional approaches is difficult and often impossible when two or more compounds pass through the detector at the same time due to lack of separation (i.e., 461 and 462). Unfortunately, the occurrence of two or more compounds passing through the detector at the same time due to lack of separation is quite a common event in many method development experiment instances.

To attempt to compensate for this limitation, often a primary goal of many HPLC method development experiments is to identify the instrument settings that result in a chromatogram with the following critical characteristics: (1) an observable peak being present for each compound in the sample, (2) situations where each peak is separated from all other peaks (i.e., no overlap) to a degree at least minimally necessary to accurately quantify the amount of the corresponding compound in the sample, and (3) the separation of a critical peak, often an API, from its nearest peak. The degree of separation between a given pair of adjacent compound peaks in a chromatogram is defined herein as the "peak resolution."

In a traditional approach to HPLC method development, the effect of instrument setting changes on the resolution of sample compounds is therefore typically relied on as being one of the most important experiment results. As a result, it is traditionally believed and practiced to carry out the following steps:

a. change one or more instrument settings, inject a sample, and obtain a resulting chromatogram;
b. associate each peak in the chromatogram with one of the sample compounds;
c. compute the peak resolution results for all adjacent peak (compound) pairs;
d. determine if the compounds are sufficiently separated, as represented by the adjacent peak pair resolution data, to accurately determine the amount of each compound in the sample to the required level of precision; and
e. repeat Steps (a)-(d) above if the compounds are not sufficiently resolved.

Unfortunately, the correct assignment of the sample compounds to the chromatogram peaks as in Step (b) above is critical to accurately interpret experiment trial results in accordance with traditional practice. Such traditional practice characteristics may include current numerical analysis approaches and the like. Since, as is often the situation, current analysis and interpretation approaches target the interactions of each compound with the HPLC system elements that result from the specific chemical and structural nature of the compound, determining specifically and precisely which compound each resolution result associates with, in a given chromatogram, is effectively the only way to track the effects of instrument changes on the separation of that compound.

A further complication especially common to early HPLC method development experiments that involve analytical column and pH screening has been that it may not be readily determinable as to how many compounds are in an experimental sample, and therefore how many peaks an experimenter is to expect in a chromatogram obtained from sample analysis by HPLC. This particular complication is further illustrated by comparing FIG. 4C with FIG. 4D.

FIG. 4D is a chromatogram 470 obtained from the same sample of FIG. 4C as analyzed under different trial settings of the HPLC instrument. The chromatogram of FIG. 4D shows twelve well separated peaks being visible along the X axis time interval of 10 to 34 minutes (see for example representative peaks at 471 and 472, where an uncertain or undefinable number of peaks exist in this same interval in FIG. 4C (see for example representative points at 461 and 462).

However, additional complications can result even where the number and identity of all compounds in a test sample are known as such knowledge does not necessarily simplify the work of correctly associating each peak with a sample compound in each trial chromatogram, since instrument changes between trials can affect both peak shape (i.e., broad-flat versus narrow-spiked) and the column transit time of the corresponding compound (i.e., peak retention time).

For example, for a particular experimental trial, a peak arising in a resulting chromatogram corresponding to a given compound may occur at 15 minutes and appear narrow and spiked. In a second trial with different instrument settings, the peak corresponding to the same compound may occur at 12 minutes and may appear as being broad and flat. Contradistinctively, a third trial's settings may cause a second peak to also occur at the 12 minute location in the chromatogram resulting in a combined peak that differs greatly in shape and area from the others. By further example, in FIG. 4C at 461, overlapping peaks corresponding to incompletely separated compounds can be seen, and again at 462, while peaks with the same or very similar shape and area in FIG. 4D occur at approximately 22, 23, and 24 minutes (473, 474, and 475 respectively).

EXEMPLARY EXPERIMENTAL DATA

FIG. 13 is a table that presents a data set from an experiment to develop a HPLC method for a drug product sample containing two APIs and several impurities. In the data set of FIG. 13 the peak resolution responses are used directly in data analysis according to the current practice (i.e., traditional) approach. As used herein, it is understood that the standard calculation of resolution for a given compound represents the normalized distance (i.e., degree of separation) of the compound's peak from the peak directly in front of it in the solvent stream, which corresponds to the peak directly to the left of the subject in the chromatogram, since that peak has an earlier X-axis time point. Therefore, for example, in the data set presented in FIG. 13, the "3—Resolution" column response represents the degree of separation of Compound 3 from Compound 2 (where Compound 2 is the compound directly ahead of it in the solvent stream). Similarly, the "4—Resolution" column response represents the degree of separation of Compound 4 from Compound 3, and the remaining columns of FIG. 13 are similarly defined.

As becomes apparent from FIG. 13, notably absent are numerous resolution result values in the data set for Compounds 3 and 4a—two impurities that must be able to be separated from Compounds 4 and 5, the two APIs in this drug product sample. The trials in which the resolution values for these impurities are missing correspond to instrument settings which were unable to separate the impurities from the APIs. This assessment is visible for Compound 4a when compared with the chromatograms in FIGS. 4E and 4F, which correspond to the results obtained from two distinct experiment trials, 11 and 12 respectively, as identified in FIG. 13. FIG. 4E is a chromatogram 479 resulting from an experiment run of trial 11, of which there is no peak corresponding to Compound 4a therein. FIG. 4F is a chromatogram 485 resulting from an experiment run of trial 12.

FIG. 4G is a chromatogram 490 resulting from an experiment run of trial 22. By comparison of FIGS. 4F and 4G, the differences between the chromatograms illustrate an entirely different kind of inherent data loss that also severely compromises the current practice approach. In this comparative assessment, both trials represent instrument conditions in which Compound 4a is resolved. However, the resolution result in trial 12 (FIG. 4E) is a measure of the separation of Compound 4a from Compound 3; while in trial 22 (FIG. 4F) the result is a measure of Compound 4a separation from Compound 5 (in part due to Compounds 3 and 5 overlapping in this particular trial).

Unfortunately, this type of resulting change in what the data represent across trials, which represents inherent loss in terms of information content of the data, is a common consequence of the change in peak locations in response to the changing instrument settings, and represents a challenging problem.

The result of inherent data loss in HPLC method development experimental work is that the data typically do not accurately represent a compound's actual chemistry-based behavior, and, as a consequence, provide doubt towards legitimate analysis and accurate interpretation of the results. This impact to the integrity of the results is further observable via regression analysis (equation-fitting) of the Compound 4a data, the results of which are set forth in FIG. 14. FIG. 14 is a table of the key regression statistics obtained from linear regression analysis of the FIG. 13 study factor data and associated compound 4a Resolution results.

For instance, the R2-Adj. (see "Adj. R Square") in FIG. 14 is the critical measure of equation predictive accuracy. The value of 0.0639 in FIG. 14 is not statistically different from zero, thereby meaning that the equation has no or questionable predictive accuracy. However, the study parameters included Column Type (e.g., two very different columns) and a wide range of Final % Organic (i.e., the gradient endpoint percent organic solvent)—two instrument parameters known to greatly affect compound separation under almost all conditions. Additionally, the observed changes in the resolution data across trials are substantially greater than can be accounted for by HPLC operating error.

Therefore, it can be and is readily determined that inherent data loss is often the cause of the inability to derive statistically valid results from numerical analysis of current practice data.

The problems described here are systemic to current HPLC method development experiment practice. In part the complications and limitations of the traditional approach start the method development process by studying the factors known or expected to have the greatest affect on peak shape and compound retention time, and therefore peak separation. However, this traditional approach results in changes that make correct compound assignments between trials extremely difficult and challenging. As a result, critical information sought from the experiment is normally not readily available due to the limitations inherent in the practice itself.

SUMMARY OF THE INVENTION

The present invention addresses such a need and sets forth an approach to solve these issues by deriving unique surrogate response data from experiment results which, in the case of the HPLC method development example just described, eliminates the need for assigning sample compounds to chromatogram peaks in each experiment trial, thereby eliminating the inherent data loss associated with the current practice.

A system and method for automatically deriving unique surrogate response data from experiment results in which inherent data loss occurs in a sufficient number of the samples to disallow quantitative effects estimation at the experimenter's desired level of confidence for statistical significance is disclosed.

In part, the unique surrogate response data sets generated by the present invention have four primary characteristics including: each is numerically analyzable; each may be more readily or directly obtained than the current practice results data in which inherent data loss occurs; each provides a response value for an experiment trial; and each provides information on the effect of a change made to the process or system that would have been obtainable if the experiment samples had had no inherent data loss.

In one embodiment the present invention is an automated system for reducing inherent data loss associated with experimentation which automatically derives one or more unique surrogate response data for experimentation. The system comprises an automated experimentation platform (AEP) for automating one or more experimentation processes, a generalized exchange module (GEM) for automating data exchanges between the said AEP and one or more target applications and for enabling the data exchange to be generic with one or more attached components including any of instrumentation, device, software application or ICP, and a means for selectively predetermining study factors for said experimentation.

In a preferred embodiment, the present invention is utilized with an HPLC system. In this preferred embodiment, the present invention is a method for reducing inherent data loss associated with experimentation comprising automatically deriving one or more surrogate response data for a defined set of experimentation having the steps of: automating one or more discrete experimentation process steps; automating data exchanges between an AEP and one or more target applications, for enabling the data exchange to be generic with one or more of any attached components inclusive of any hardware, software, HPLC system, software applications and ICP, and generating surrogate responses in relation to controllable parameters in relation to study factors for said experimentation.

In a further preferred embodiment the method additionally includes further the step of executing a second experimentation trial in which the study factors used in the first experiment are held constant at the level settings defined as optimum by analysis of that experiment's Trend Response data set.—The second experimentation trial is conducted so as to further optimize the HPLC instrument analytical method.

In yet another preferred embodiment a computer readable medium containing program instructions is provided to implement the present invention.

As a foundation, the system in an aspect of the present invention, comprises an automated experimentation platform (AEP) with a device setup interface that imports device setup and control definitions and allows user configuration and editing of the definitions, an experiment setup interface that is dynamically configurable to specific experiment types and their target instrument platforms and devices, and allows user final configuration and editing of all experiment setup settings, a reporting setup interface that dynamically builds reports from data and results and allows user configuration and editing of the reports, a design of experiments (DOE) engine that generates statistically valid and rigorous scientific experiments and sampling plans tailored to the target devices, including any software program for controlling the devices (ICP); and a generalized exchange module (GEM) for automating data exchanges between the AEP and one or more target applications and for enabling the data exchange to be generic.

Through the use of the automated experimentation platform (AEP) and generalized exchange module (GEM) data exchange is automatically provided between the DOE engine and the instrument, device, or ICP; and through the generalization of the exchange module the data exchanges can be adapted to any external software application, instrument, device, or ICP. Therefore, configuring of any scientific experiment type, control of any instrument or device, reporting of any data and results, and data exchanges between external software applications, instrument platforms, and devices can be achieved by the AEP and GEM automation components of the invention.

BRIEF DESCRIPTION OF THE DRAWINGS

FIG. 4A demonstrates the adaptation of the general process flow diagram 300 of FIG. 3 to that of an HPLC.

FIG. 13 is a table that presents a data set from an experiment to develop a HPLC method for a drug product sample containing two APIs and several impurities.

FIG. 14 is regression statistics for compound 4a.

FIG. 15 presents some of the Trend Response data computed in an experimental use scenario of the present invention implementing Fusion AE from the HPLC method development experiment discussed previously.

FIG. 16 presents the regression analysis results for the Total Peaks trend response.

FIG. 17 presents the regression analysis results for the Resolved Peaks (>1.50) trend response.

DETAILED DESCRIPTION

Abbreviations and Acronyms

Figure 1:
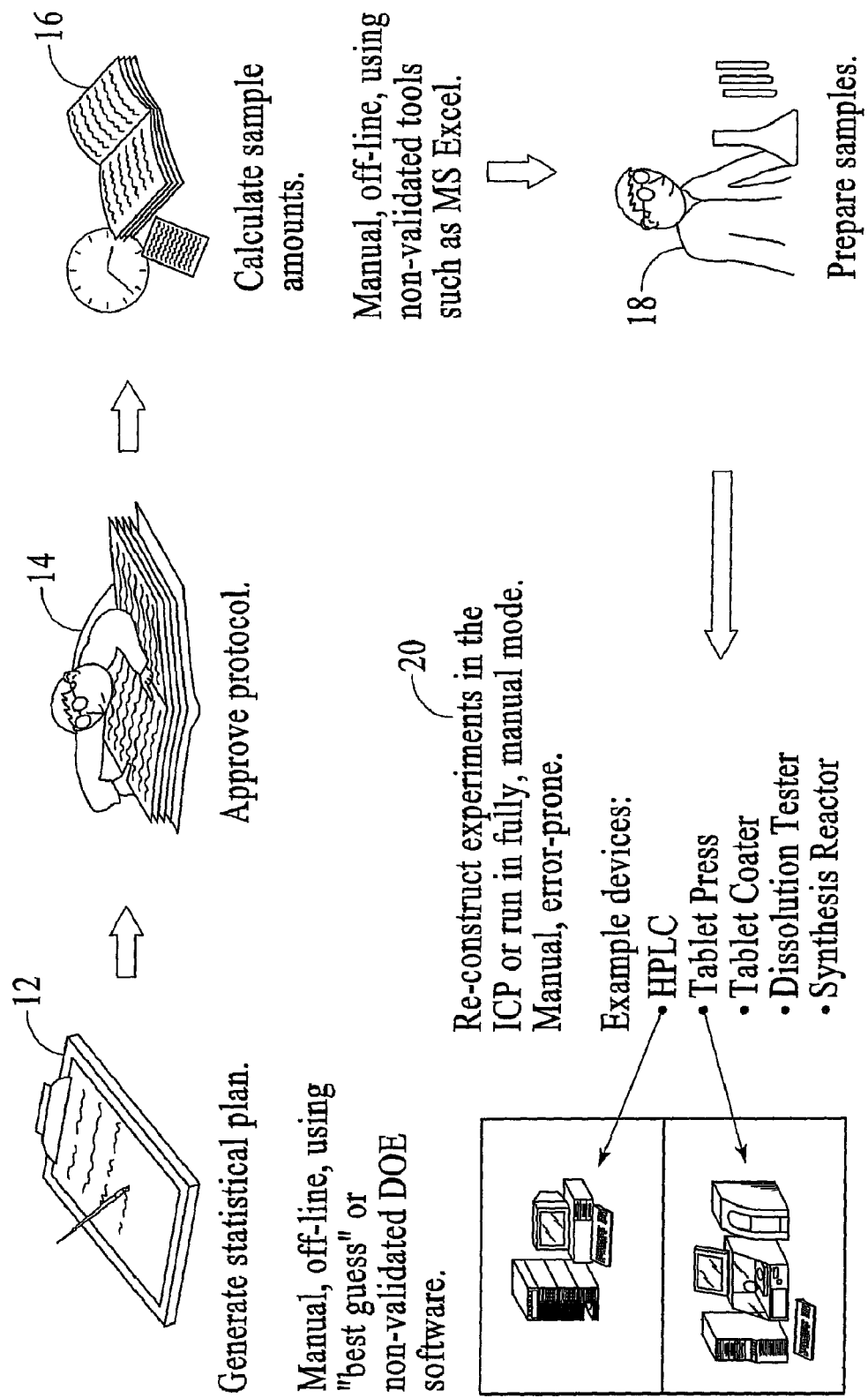
FIG. 1 illustrates the manual tools and operations involved in designing a research, development, or engineering experiment.
Figure 2:
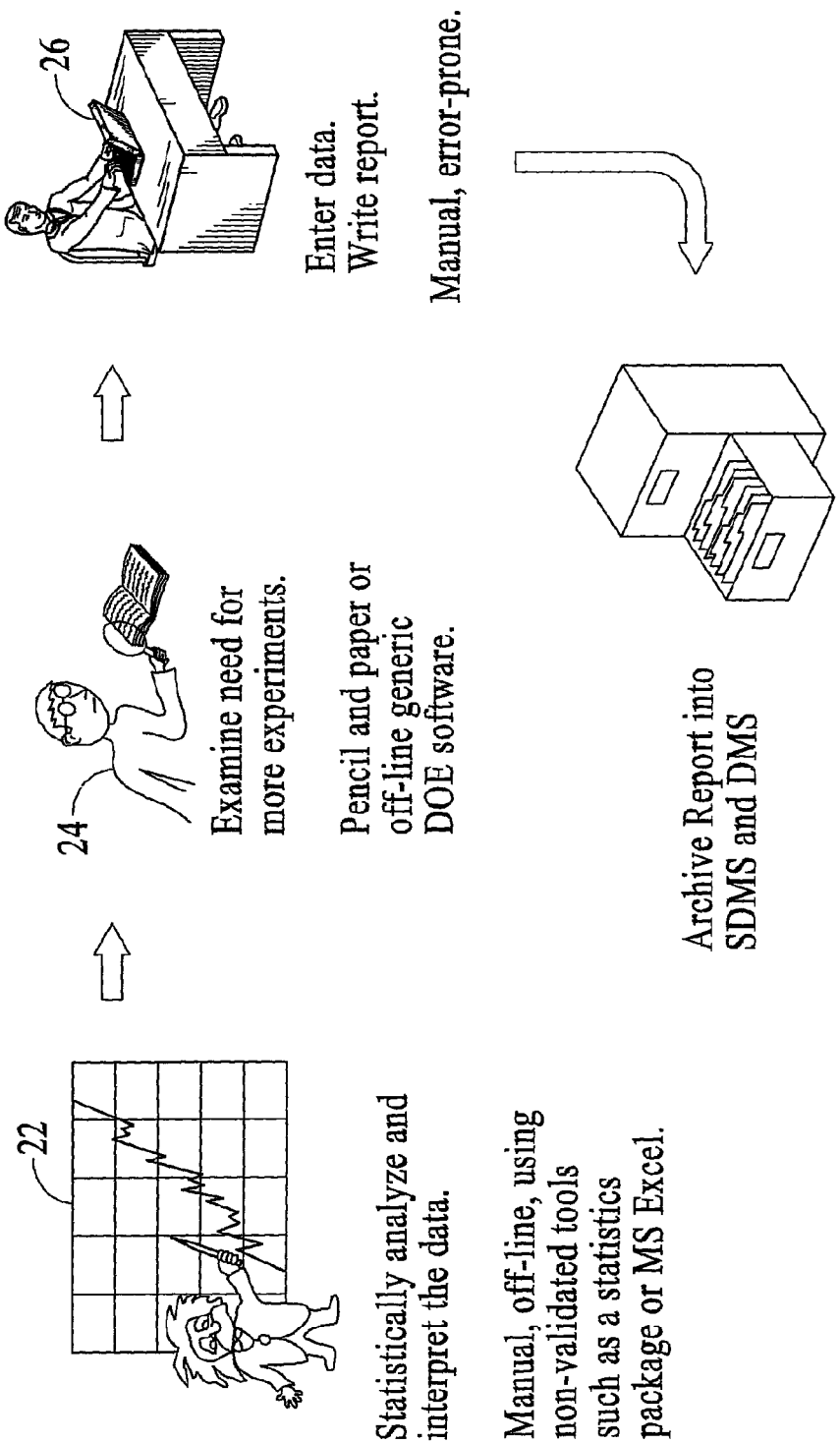
FIG. 2 illustrates the manual tools and operations involved in analyzing the data and reporting the results of a research, development, or engineering experiment.
Figure 3:
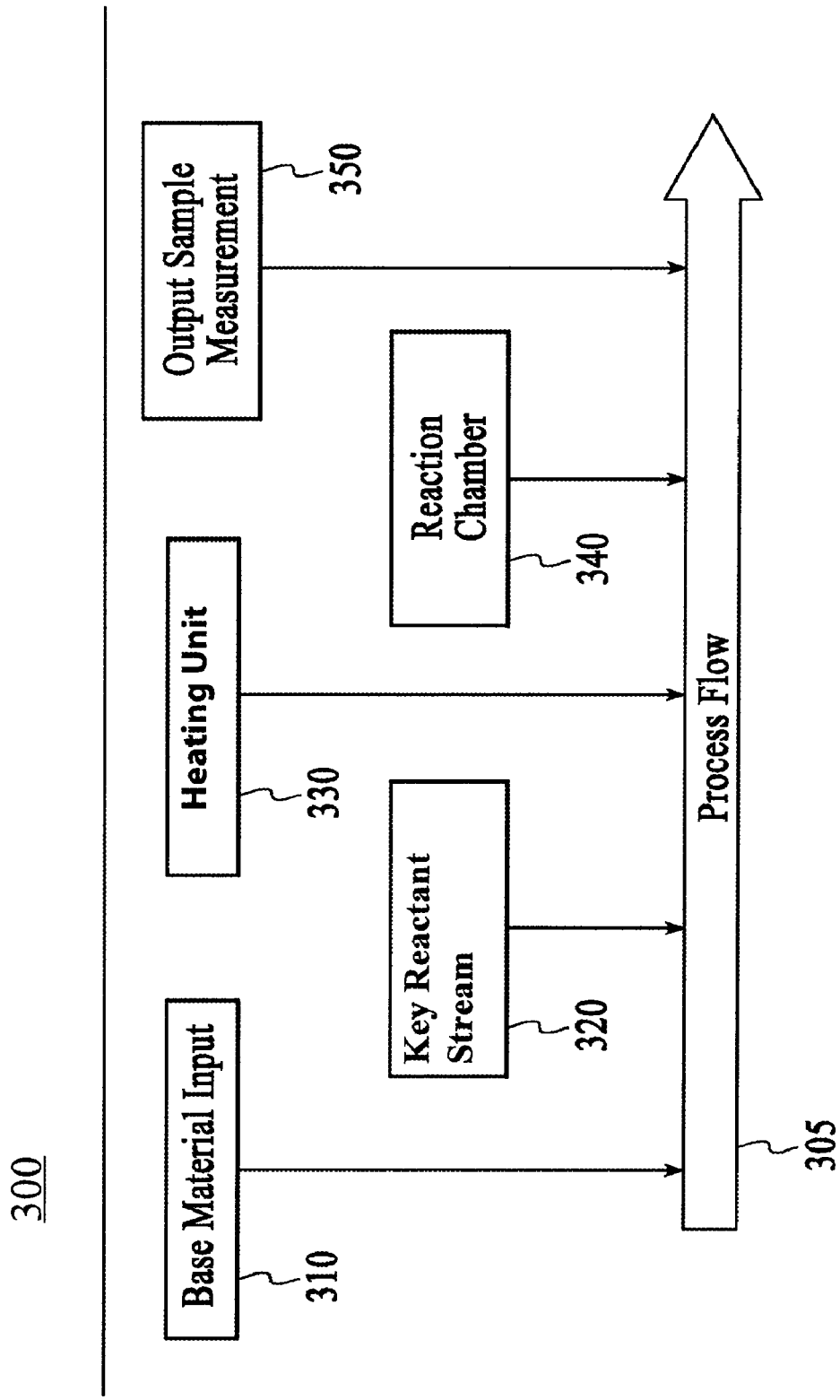
FIG. 3 illustrates a generalized flow diagram of a process in a process flow direction consisting of four discrete elements: base material input, key reactant input, heating, and chemical reaction.
Figure 4B:
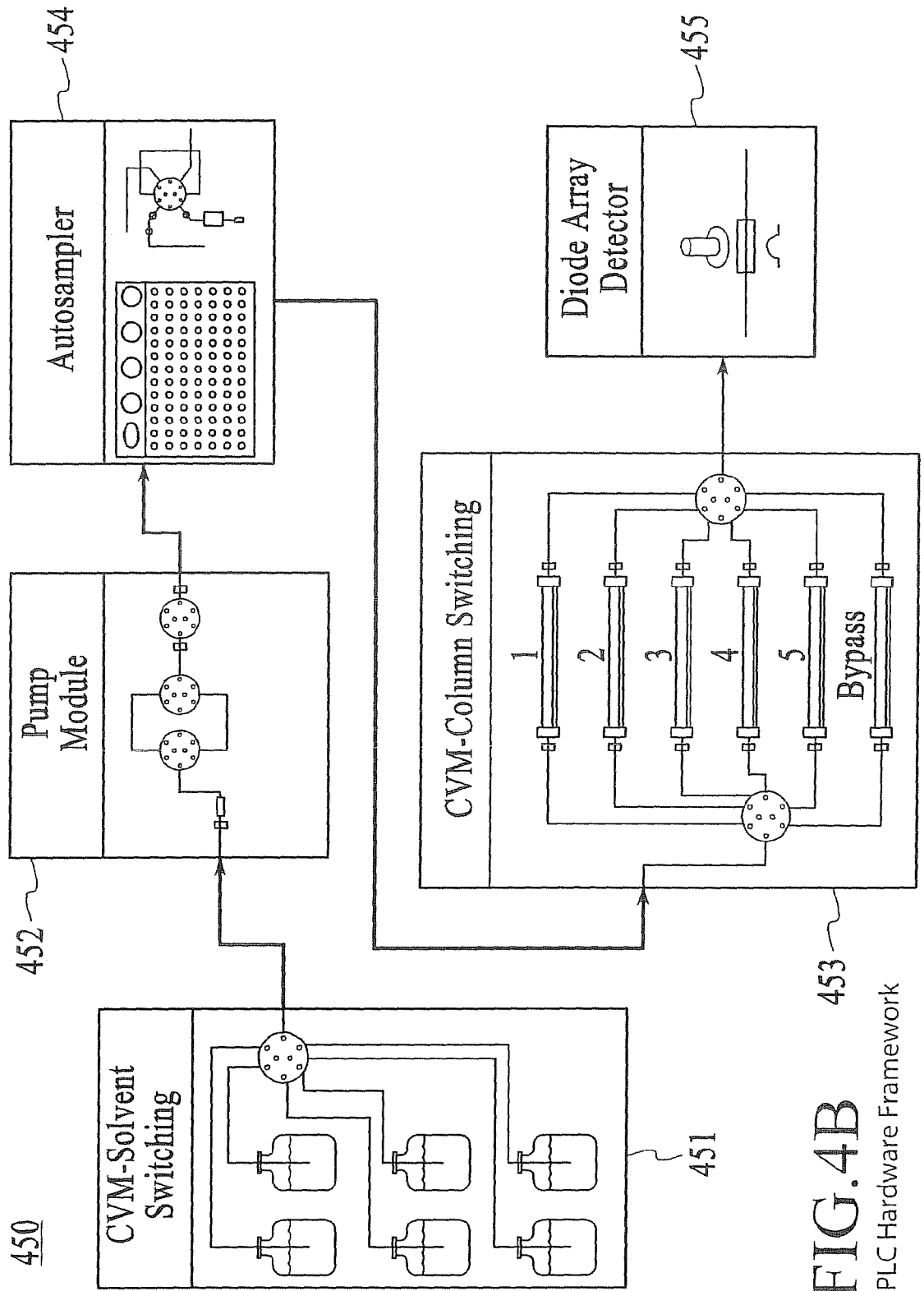
FIG. 4B depicts an instrument hardware framework associated with an HPLC instrument system.
Figure 4C:
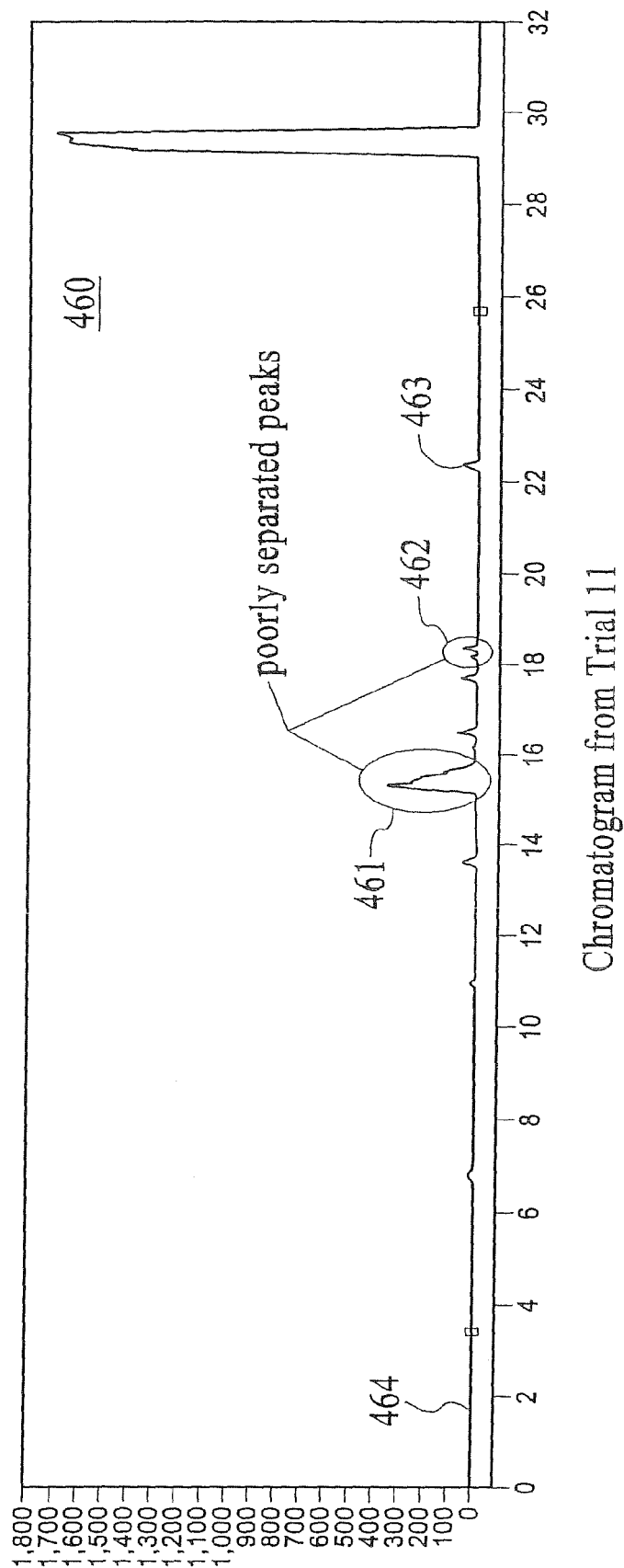
FIG. 4C depicts a graphical chromatogram representation of experimental results data obtained from a particular trial run trial in one of the experimental runs under assessment herein, wherein the "raw" results in this chromatogram are in the form of "absorbance peaks".
Figure 4D:
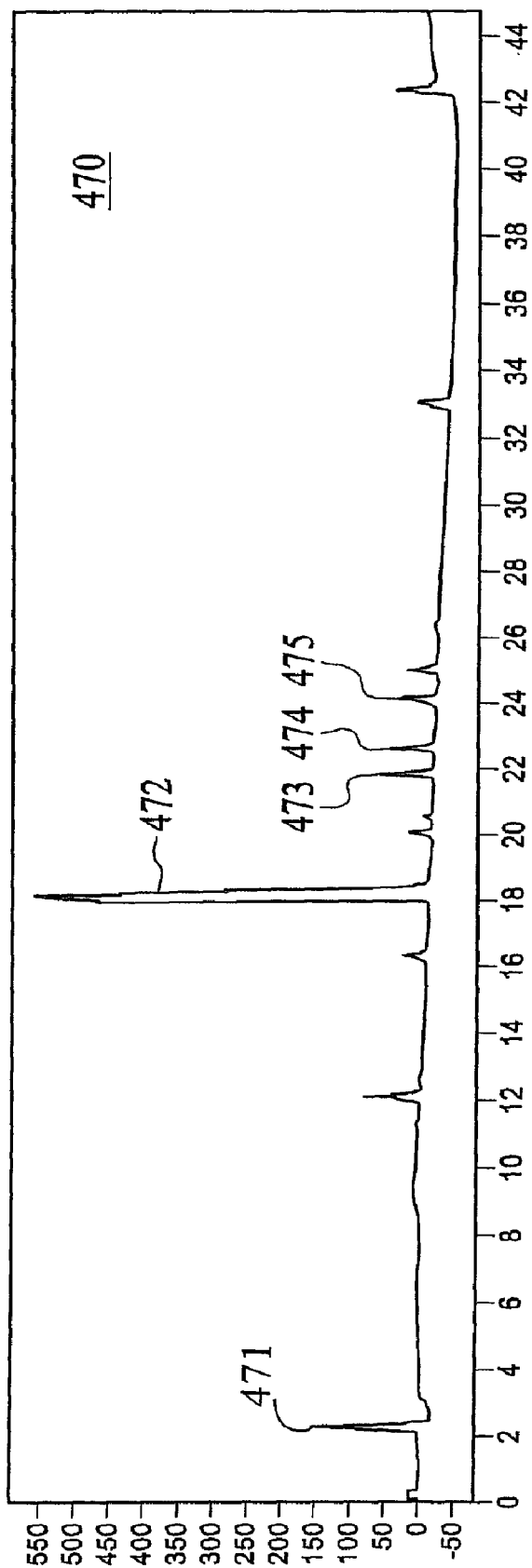
FIG. 4D is a chromatogram obtained from the same sample of FIG. 4C as analyzed under different trial settings of the HPLC instrument.
Figure 4E:
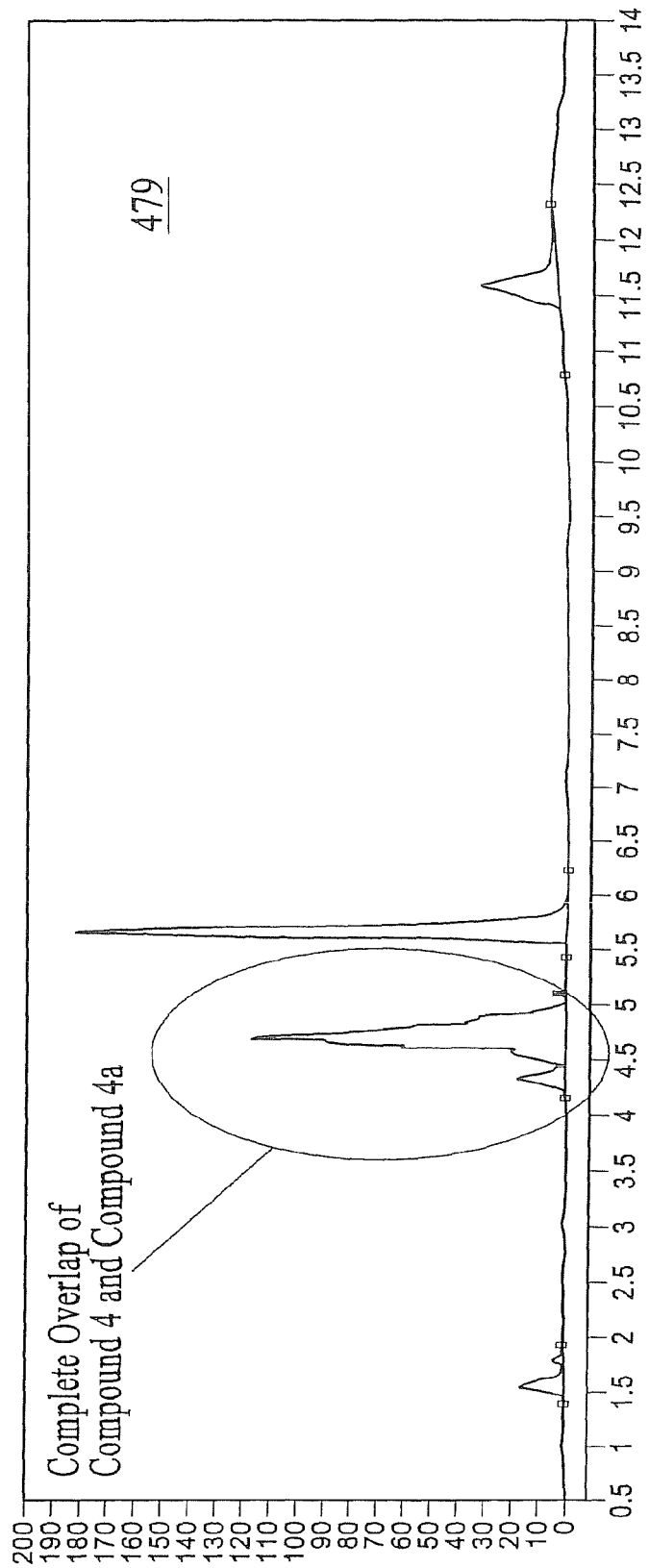
FIG. 4E is a chromatogram resulting from trial run 11 of an experiment.
Figure 4F:
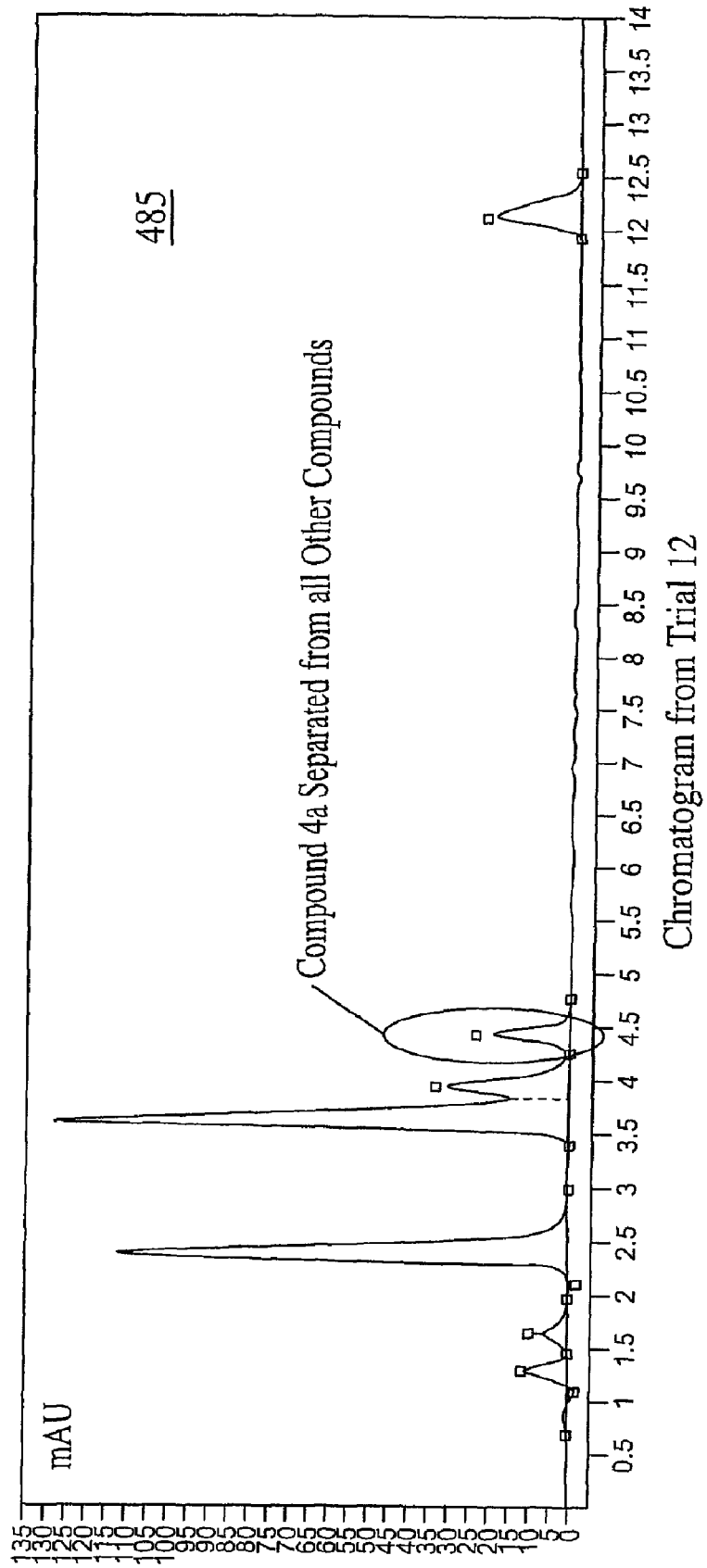
FIG. 4F is a chromatogram resulting from trial run 12 of an experiment.
Figure 4G:
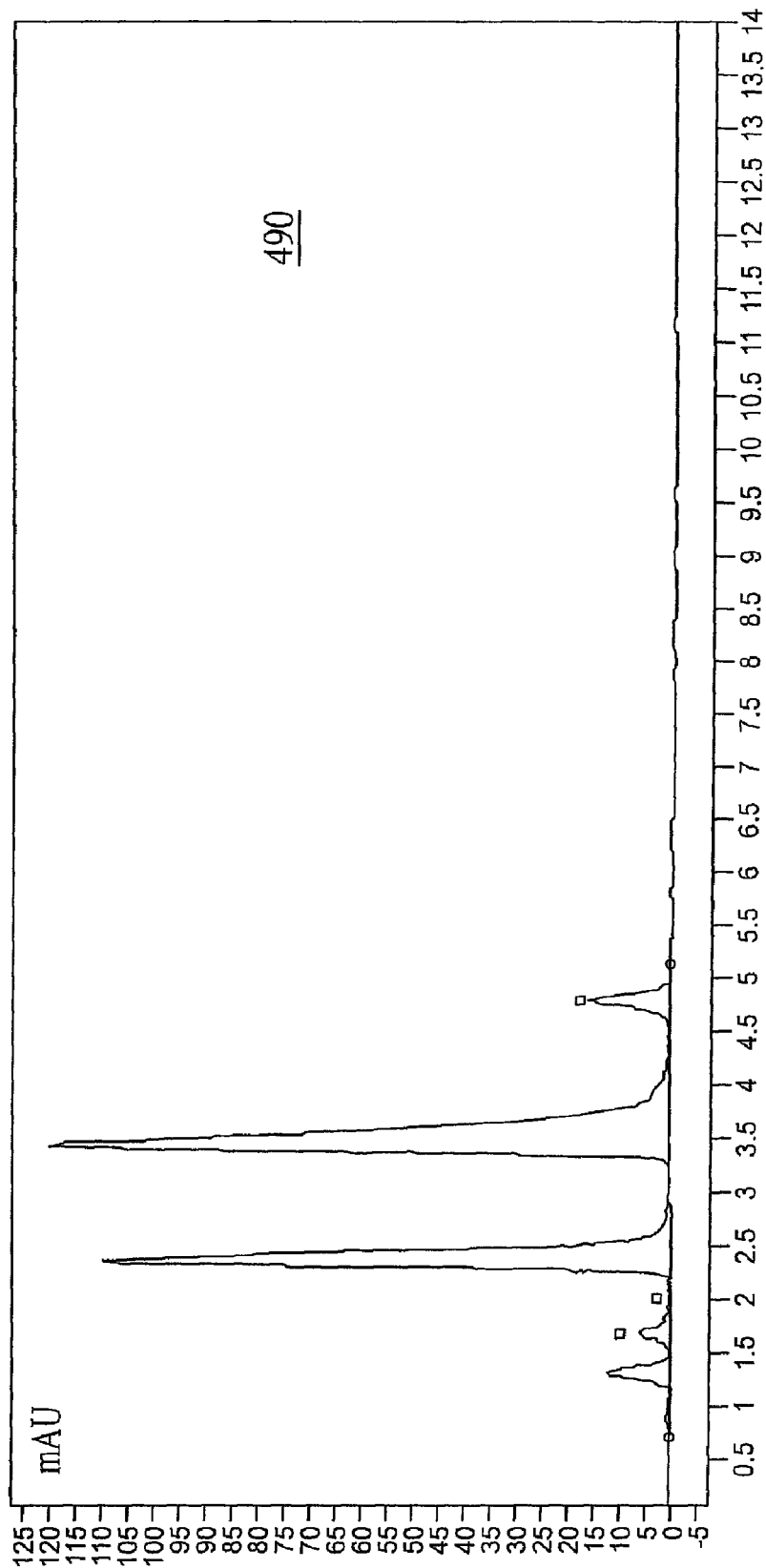
FIG. 4G is a chromatogram resulting from trial run 22 of an experiment.

AEP—Automated Experimentation Platform.

CDS—Chromatography Data System. A traditional name for an ICP (see below) that controls and handles the data from HPLC and GC instruments (see below).

DOE—design of experiments

GEM—generalized exchange module.

Device—An instrument, piece of equipment, or apparatus. Examples include but are not limited to analytical instruments, weighing and measurement devices, sampling and sample handling equipment, and processing equipment.

FDA—United States Food and Drug Administration.

GC—Gas Chromatography. An instrument-based quantitative analytical technique. GC instruments are widely used as research and development and quality assurance tools in many industries (e.g. pharmaceuticals, biotechnology, and petrochemicals).

HPLC—High Performance Liquid Chromatography. An instrument-based quantitative analytical technique. HPLC instruments are widely used as research and development and quality assurance tools in many industries (e.g. pharmaceuticals, biotechnology, and petrochemicals).

ICH—International Conference on Harmonization of Technical Requirements for Registration of Pharmaceuticals for Human Use.

ICP—instrument control program. The software program that operates a device.

Programmatic Interface—A software based communication channel that allows software programs to exchange instructions and data.

SDK—Software Development Kit. An SDK is a published programmatic interface for a device or a device's ICP.

XML—eXtensible Markup Language. A metalanguage written in SGML that allows one to design a markup language, used to allow for the easy interchange of documents on the World Wide Web.

XML Schema—XML Schemas express shared vocabularies and allow machines to carry out rules made by people. They provide a means for defining the structure, content and semantics of XML documents.

XSL—eXtensible Stylesheet Language. A language used to construct style sheets for an XML, consisting of two parts:

1. XSL Transformations (XSLT). A language for transforming XML documents.

2. XSL Formatting Objects (XSL FO). XML vocabulary for specifying formatting semantics.

XSL Transformation—The set of XSL templates applied to XML data to transform it into another format.

XSL File—The file that contains the XML Transformation.

XSD File—XML Schema Definition is a language for specifying the grammar of the markup allowed in an XML file. Such a specification is called a schema and typically has a file extension of XSD.

The present invention relates generally to scientific research, development, and engineering experiments and more specifically to providing a system for automated experimentation. The following description is presented to enable one of ordinary skill in the art to make and use the invention and is provided in the context of a patent application and its requirements. Various modifications to the preferred embodiments and the generic principles and features described herein will be readily apparent to those skilled in the art. Thus, the present invention is not intended to be limited to the embodiments shown, but is to be accorded the widest scope consistent with the principles and features described herein.

In one aspect, foundationally, a system and method in accordance with the present invention provides for full automation of research, development, and engineering experimental work. The present invention in such an aspect provides for:

1. Creating and exchanging device setup and control definitions, experiment type definitions, analysis definitions, reporting definitions, and user addressable configuration and control of the definitions.

2. An experiment setup interface that dynamically configures to specific experiment types and their target instrument platforms and devices.

3. Automating data exchange between a design of experiments (DOE) software engine and any targeted software application, instrument, device or ICP.

4. Making the data exchange technology generic and adaptable to any targeted software application, instrument, device, or ICP.

Aspects of the present invention utilize the automated experimentation process disclosed in U.S. patent Ser. No. 11/262,539, filed on Oct. 25, 2005, entitled "System for Automating Scientific and Engineering Experimentation," which is incorporated herein by reference.

To describe the features of the present invention in more detail, refer now to the following description in conjunction with the accompanying Figures.

Overview

An automated experimentation (AE) system in accordance with the present invention is a proprietary software platform for automated experimentation. In a preferred embodiment, the AE system comprises a software program with statistical and mathematical informatics engines for:

Design of experiments (common abbreviations: DOX, DOE)
Numerical data analysis
2D, 3D, and 4D (trellis) visualization graphics
Multiple response optimization
Formal reporting The AE system also includes tools for regulatory (FDA, ICH) compliance, workflow management control, application-specific experimentation, and file-less data exchange with targeted software applications, instruments, devices, or ICPs.

The AE system exports experiment designs to targeted software applications, instruments, devices, or ICPs as ready-to-run experiments in the native file and data formats of the target, imports all results from the target, analyzes and graphs the results, and creates presentation quality reports.

In a currently available example embodiment the AE system's strategic features include:

E-lab Notebook Interface—Document style interface displays reports in HTML windows. Encrypted database file format contains OLE objects for embedding a Microsoft® Word™ document and Microsoft Excel™ workbook. Externally generated graphics can be imported and embedded into all reports.

Full 21 CFR 11 Compliance Support toolset—Includes e-signature controls for all data entry and exchanges, full audit trail, and event logging.

Analysis and Reporting—Application-specific automated statistical analysis, graphing, and reporting.

Acceptance Criteria Testing—Embedded analytics automatically compare actual results with user entered "pass/fail" acceptance criteria.

Workflow Management—Construct and export work templates. Permissions and authorities control of all work.

In the pharmaceutical and biotechnology industries, current embodiments of the AE system are utilized in the mission-critical activities within analytical R&D, chemical entity development (CED), chemistry development (CRD), process R&D, formulation R&D, and manufacturing QA.

Accordingly, the AE system in an example embodiment of the present invention is a software system which utilizes custom application modules for the targeted design of experiments and the analysis, graphing, optimization, and reporting of experimental data and results in support of all drug development pipeline activities.

The AE system imports Device Driver XML files (Device XMLs) generated outside of the AE system according to a public Schema, for example an XML schema. Device XMLs contain the data that enables the AE system to set up experiments and address, control, and exchange data with one or more devices. These XML files contain the instructions that allow the AE system to address the existing interface of one or more devices or their controlling ICPs.

User generated Device XMLs enable the AE system to address and control any instrument platform, component module, or device via any public or private programmatic interface that the platform module, or device contains. No programming need be developed to adapt the existing interface of an external software program, device, or ICP to the AE system.

The AE system utilizes experiment type XML files (experiment XMLs) generated outside of the AE system according to a public Schema, for example an AE XML schema. The experiment XMLs contain the data that enable the AE system to dynamically configure the experiment setup interface to address the specific experiment type and its target devices. The AE system automatically applies an experiment setup builder XSL to the experiment XML and the device XML to generate an experiment setup XML that complies with the AE XML Schema. No programming need be developed to adapt the experiment type to the AE system. An AE graphical user interface (GUI) builder transforms experiment type settings descriptions and device descriptions into AE's dynamically configurable AE DOE GUI. The GUI displays all experiment type settings along with device control points, constraints, and graphical images of each control point, for final refinement. The AE DOE GUI enables construction of statistically designed experiments for automatic execution on the device using the final experiment type and device settings description.

The AE system utilizes analysis template XML files (Analysis XMLs) generated outside of the AE system according to a public Schema, for example an AE XML schema. The analysis XMLs contain the data that enables the AE system to dynamically select and sequence the analysis routines from its internal analysis library that are applied to data and results to generate an analysis results set template specific to the experiment type, the user requirements, and the area of application. The analysis results set can be automatically available to any report by including it into the report XML. No programming need be developed to adapt analysis templates to the AE system. An AE analysis builder transforms analysis routine and sequence settings descriptions into AE's dynamically configurable data analyzer GUI. The GUI displays all routine and sequence settings for final refinement. The data analyzer GUI enables automatic data analysis on the AE System using the final analysis settings description.

The AE system utilizes report template XML files (Report XMLs) generated outside of the AE system according to a public Schema, for example an AE XML schema. The Report XMLs contain the data that enables the AE system to dynamically configure the reporting engine to generate a report specific to the experiment type, the user requirements, and the area of application. No programming need be developed to adapt report templates to the AE system. An AE report builder transforms analysis report data and results complement and sequence settings descriptions into AE's dynamically configurable reporter GUI. The GUI displays all complement and sequence settings for final refinement. The reporter GUI enables automatic report generation on the AE System using the final report settings description.

The public XML schema enables the user to update, add to, remove, or otherwise modify the device XMLs, experiment XMLs, analysis XMLs, and report XMLs created for external software applications, instrument platforms, devices, or ICPs at any time to dynamically address changes to the target application platform, device, or ICP.

In addition, in a preferred embodiment, the AE system includes a variety of plug-in application modules—each of which generates specific types of statistically-based experiment designs as directed by experiment type XMLs and device XMLs, and executes the associated analysis, graphing, optimization, and reporting of the experiment's results, as directed by analysis XMLs and report XMLs. The user could configure and direct the application modules, for example, in a preferred embodiment, by constructing device XMLs, experiment XMLs, analysis XMLs, and report XMLs, and operate the application module tools through a series of rule-based wizards.

AE system application modules can address a wide variety of different application areas. For example, one application module is used for chromatographic analytical instrument method development while another is used for synthetic chemistry process development.

The device XMLs of the AE system also preferably contain the data that enables the AE to address, control, and exchange data with various independently conceived and separately designed target software applications, instrument platforms, devices, and ICPs via any public or private programmatic interface that the target contains.

The AE system in a preferred embodiment is an electronic signature based system for enabling software operations and subroutines and imposing management review and approve loops on user work within the AE system.

The AE system generates statistical experiment designs or user constructed experiments that can be run on the target instrument, directly or via the instrument's controlling ICP. The AE system communicates the experiments to an instrument's controlling software via file-less data transfer using the instrument's public or private programmatic interface.

In addition, driver XML files of the AE system contain several layers of data regarding constraints on controllable instrument parameters, including:
Absolute constraints: achievable setting limits.
Manager constraints: restrictions on setting limits due to current state or required practice.
Analyst constraints: restrictions based on current experiment considerations.

The AE system includes an automated experimentation platform (AEP) and a generalized exchange module (GEM) to provide a unified software platform for use in automating experiments. To describe the features of GEM and its interaction with the other AE system elements refer now to the following description in conjunction with the accompanying Figures.

Overview—Generalized Exchange Module (GEM)

The generalized exchange module (GEM) is a proprietary software-based technology that enables a software program to dynamically configure its user interface and directly control a device and/or directly address the device's ICP—whether or not the device's target programmatic interface is published in an SDK. The level of control that can be provided by GEM is only limited by the level of device addressability provided by the device's programmatic interface. GEM accomplishes this through the following program elements:

GEM XML schema by which users can completely describe for any ICP:
All controllable elements of a device (modules and sub-modules).
Graphical images of each device element.
Individual control points of each device element.
Dependency relationships between elements and control points of a device.
Constraints (limits and other restrictions) on the allowable settings of control points.
Programmatic commands, addresses, and data paths for controlling the device.
Programmatic commands, addresses, and data paths for retrieving data from the device.

The following components are utilized in a preferred embodiment of a GEM:
An ICP importer that transforms an ICP's native device descriptions into GEM's native data structure.
A template importer that transforms experiment type settings descriptions, analysis settings descriptions, and report settings descriptions into the AEP's native data structure.
A GEM GUI builder that transforms device descriptions into GEM's dynamically configurable GEM ICP GUI. The GEM ICP GUI displays all device control points and constraints, including graphical images of each control point for further refinement and restriction of the device description.
A design of experiment (DOE) exporter that writes the control point settings of the statistical experiment design or user constructed experiment to the device.
A DOE importer that reads experiment result output data from the described device.

Function of GEM
Transforming an ICP's native device descriptions into GEM's native data structure.
Displaying all device control points and constraints, including graphical images of each control point via a configurable ICP user interface.
Transforming experiment type, analysis, and reporting settings descriptions into the AEP's native data structure.
Indirect or direct control of a device and/or direct addressability of the device's ICP whether or not the device's target programmatic interface is published in an SDK.
Writing control point settings to a device or the device's ICP as ready-to-run experiments in native file and data formats using file-less data transfer protocols.
Reading data from a device or the device's ICP using file-less data transfer protocols.
Converting a user analysis template into a customized analysis template that auto-completes when the data are automatically retrieved from a device or the device's ICP via a dynamically configurable reporting interface.
Converting a user reporting template document (Microsoft Word, RTF, TXT, or HTML) into a customized reporting template that auto-completes when the data are automatically retrieved from a device or the device's ICP via a dynamically configurable reporting interface.

AEP with GEM—Operational Flow Diagram

Figure 5A:
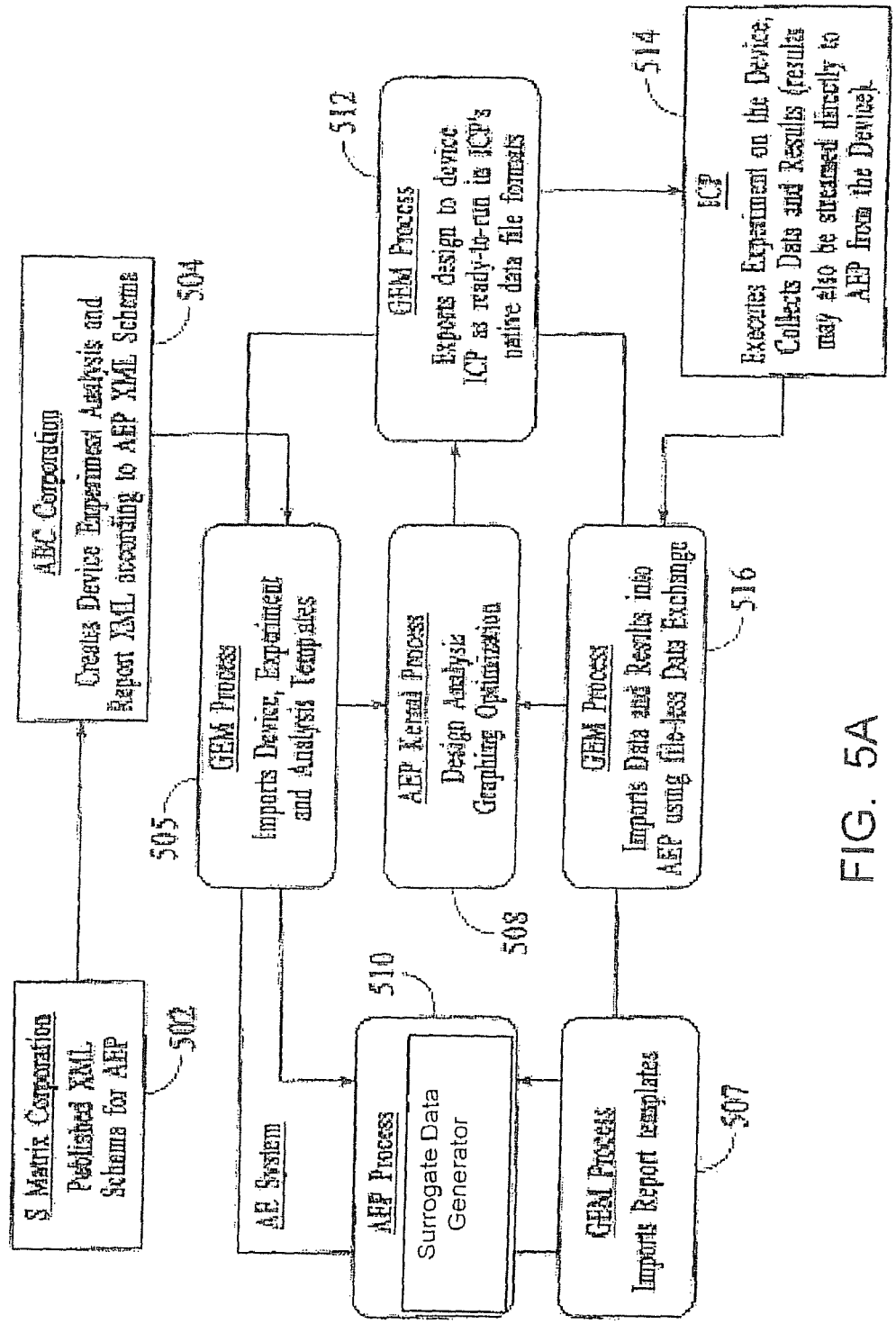
FIG. 5 provides an automated experimentation platform (AEP) and generalized exchange module (GEM) operational flow diagram illustrating (1) XML-based data exchange with a third-party company as one mechanism of fileless data exchange, and (2) resulting AEP process flows for the surrogate data generator with an instrument control program (ICP), in a preferred embodiment of the present invention.
Figure 5B:
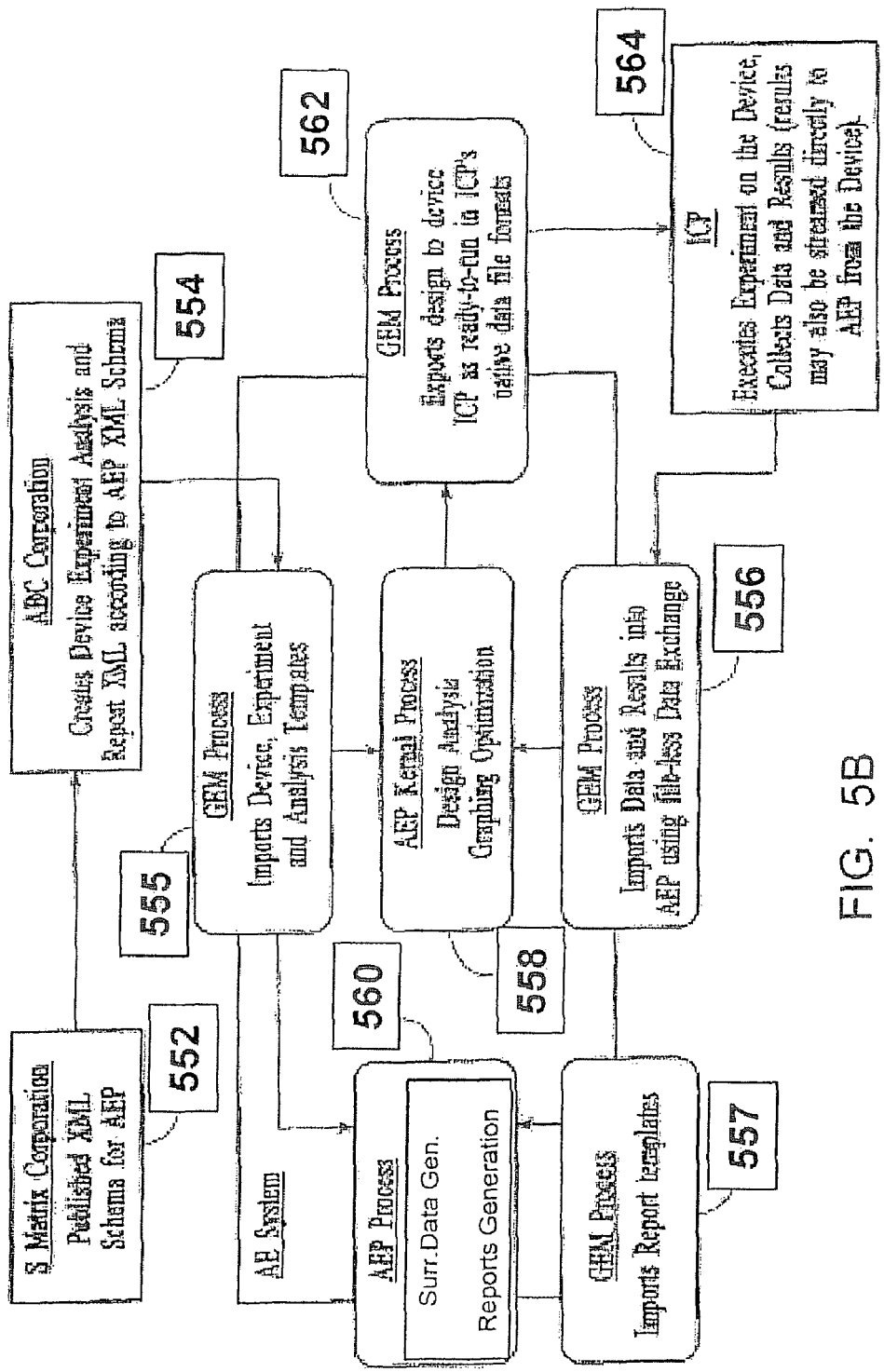

FIG. 5A presents an AEP and GEM operational flow diagram illustrating (a) XML exchange with a third-party company, and (b) resulting AEP for the surrogate data generator and GEM process flows with the instrument company's ICP, in accordance with a preferred embodiment of the invention. Referring to FIG. 5A, the flow diagram illustrates that company 1 (S-Matrix Corporation) publishes XML schema for the AE system, via step 502. Then a device company, for example, ABC Corporation, creates experiment, analysis, and reporting settings AE XMLs and device description ICP XMLs according to the AE system XML schema, via step 504. A GEM process imports device, experiment and analysis templates, via step 505. A GEM process may import report templates, via step 507. The AEP kernel process carries out design, analysis, graphing and optimization, via step 508. The GEM process then exports design to the ICP as ready-to-run in ICP's native data/file formats, via step 512. The ICP executes the desired experiment on the instrument, and collects results data (results may also be streamed directly to AE system from the device), via step 514. The ICP then sends the data and results to the GEM process, which imports the data and results to the AE system using file-less data exchange, via step 516. The AEP kernel processes carry out analysis, graphing and optimization, again via step 508. The AEP process then produces surrogate data via the method of the present invention, as a surrogate data generator, including the use of integrated peak data, via step 510.

AEP with GEM—Software Installation Configurations

Figure 6:
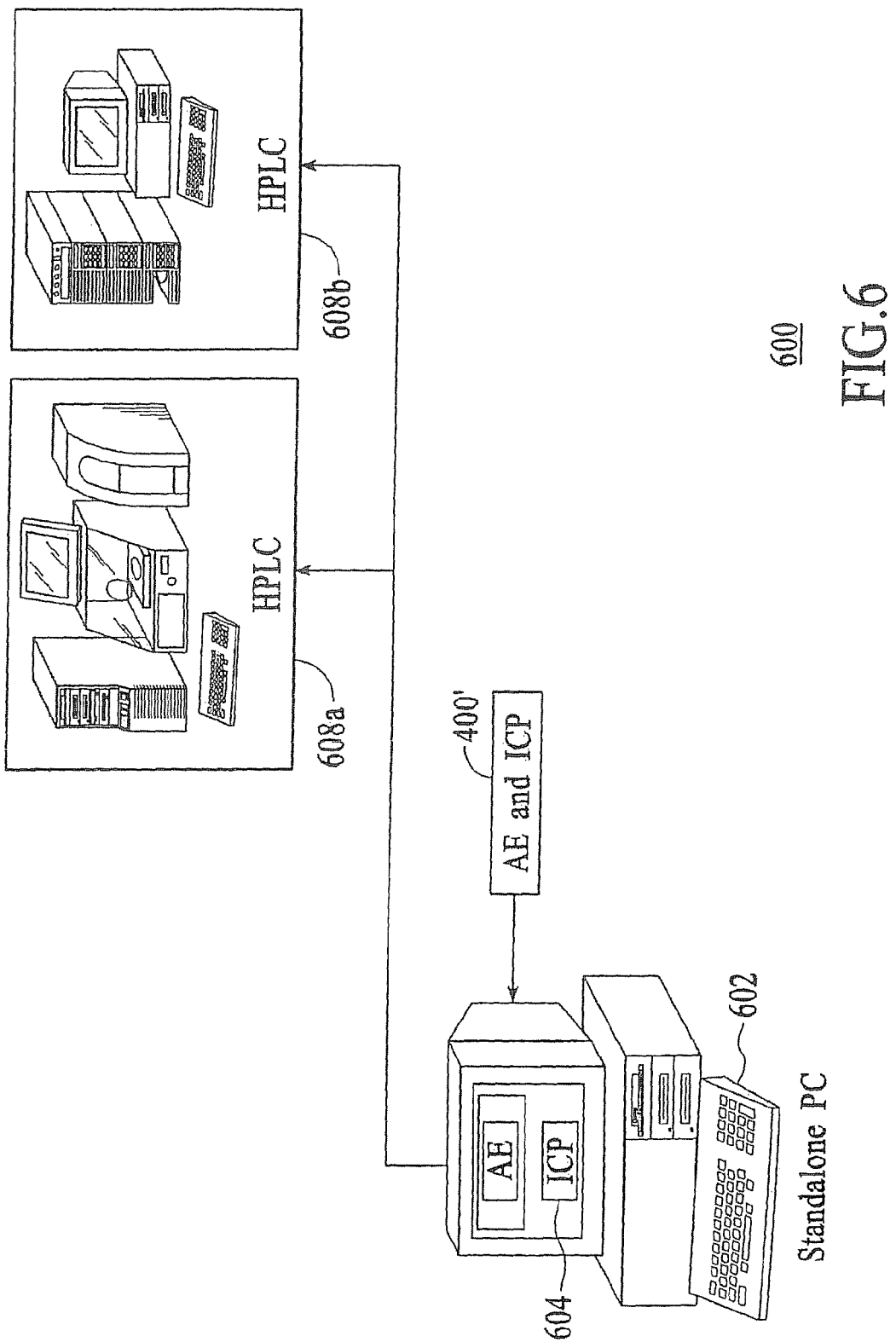
FIGS. 6-8 show different software installation configurations of an automated experimentation system with an ICP.
Figure 7:
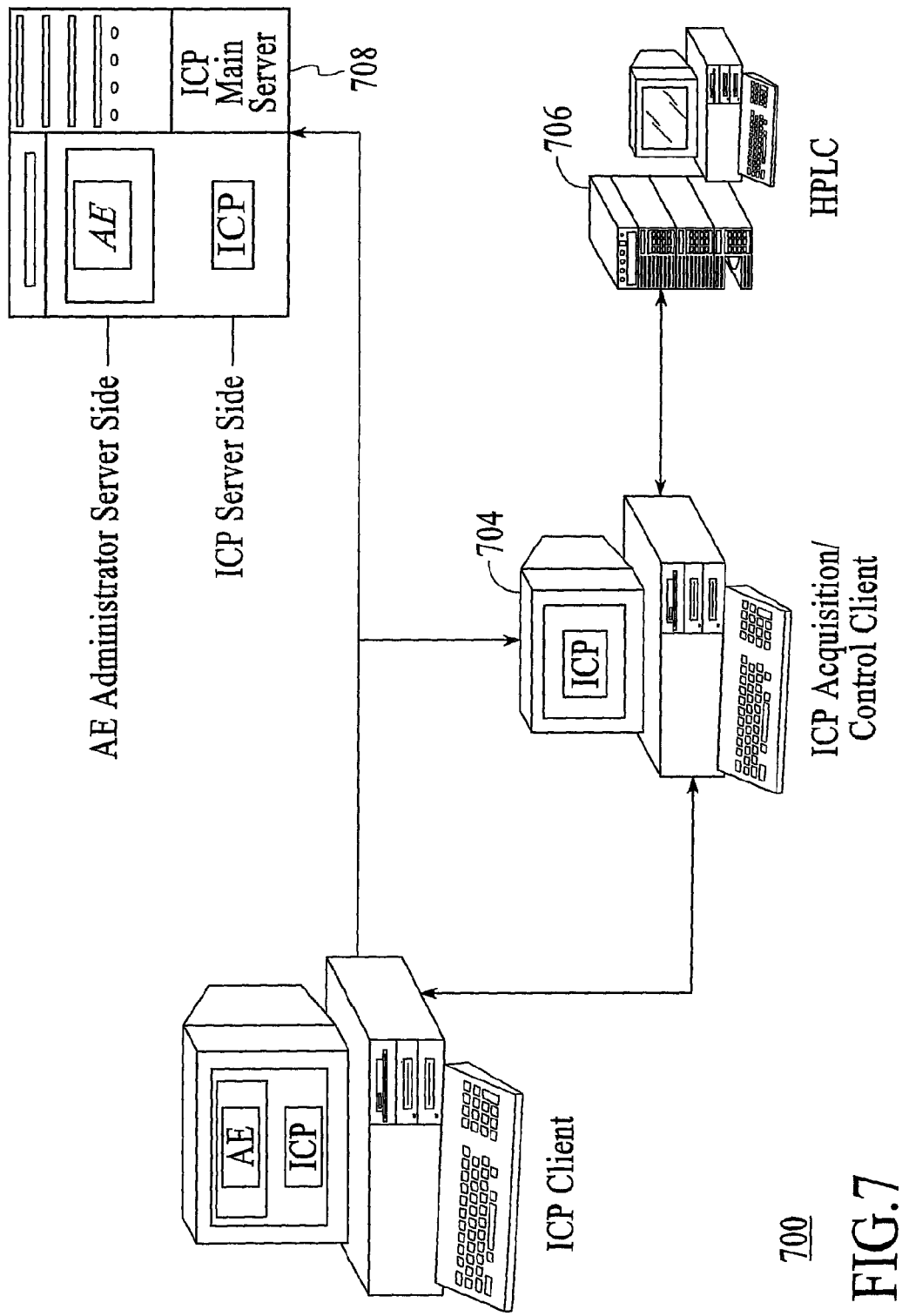
Figure 8:
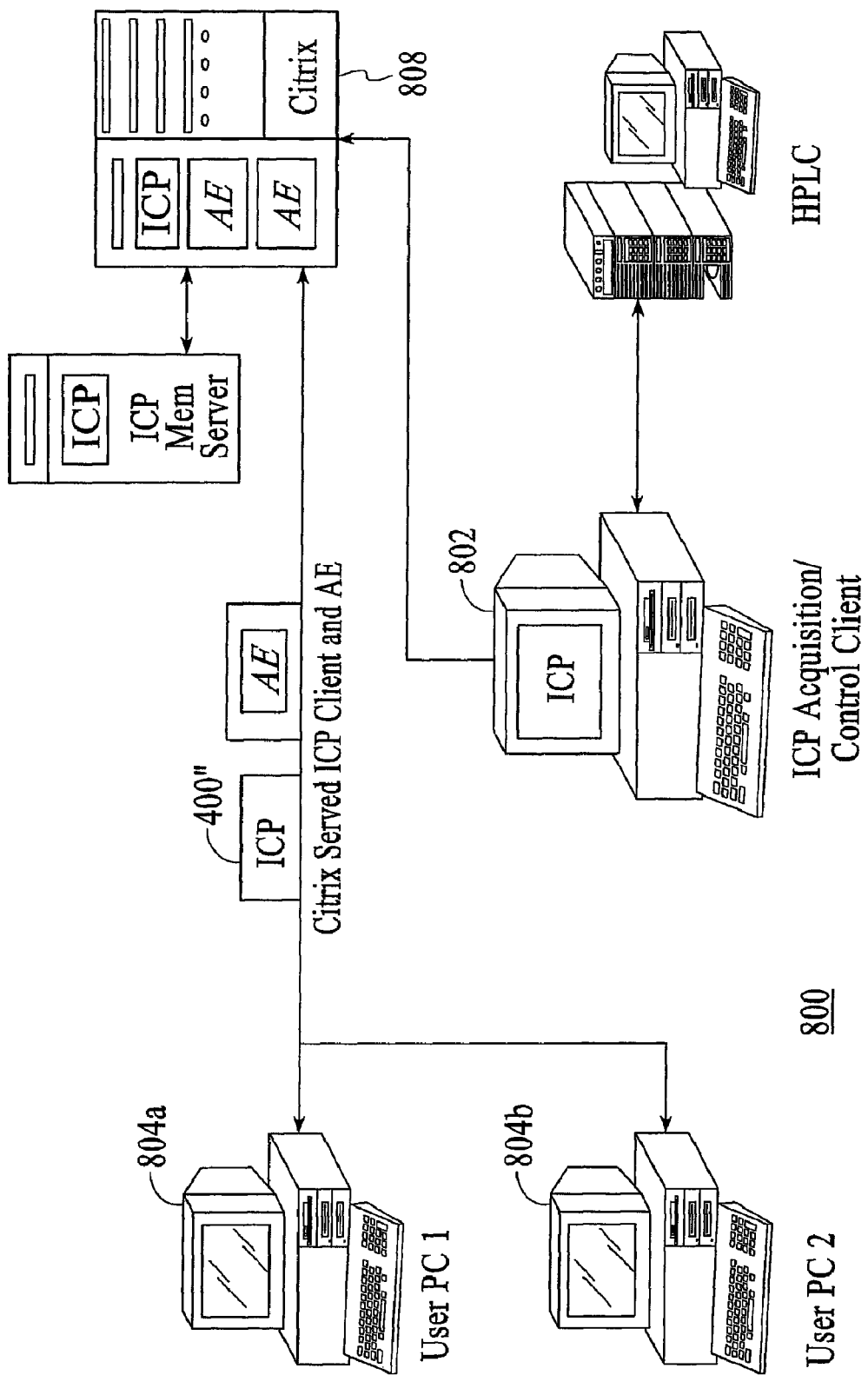

FIGS. 6-8 show different software installation configurations of the AE system (AEP and GEM) with an ICP. FIG. 6 shows a standalone workstation configuration 600. The standalone workstation configuration 600 includes a standalone PC 602 linked to the ICP 604, the servers 608a and 608b, and the AE system and ICP 400'. FIG. 7 shows a network configuration 700 in which the ICP is a Client/Server (C/S) application 704, linked to the ICP main server 708 and to another server 706. FIG. 8 shows an alternative network configuration 800 in which the ICP is a C/S application 802 and both the AE system and the ICP 400" are served to user PCs 804a and 804b via a client application such as the Citrix® MetaFrame application 808.

Accordingly, AEP and GEM cooperate to automate the formerly manually intensive research, development, and engineering experiments. To illustrate this in more detail refer now to the following discussion which is based on one target application area using an example embodiment in accordance with the present invention in conjunction with the accompanying figures.

Figure 9:
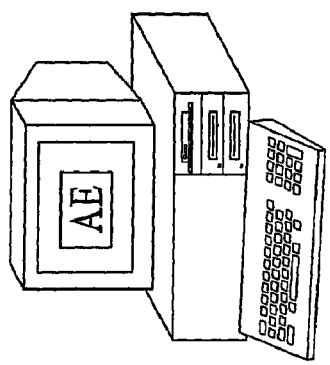
FIG. 9 illustrates the research, development, or engineering experiment workflow previously presented in FIG. 1 adapted to an HPLC method development experiment created within the automated experimentation system and automatically transferred to an instrument's ICP.
Figure 9:
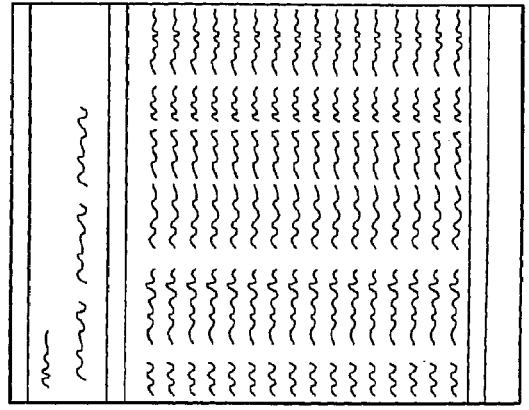
Figure 9:
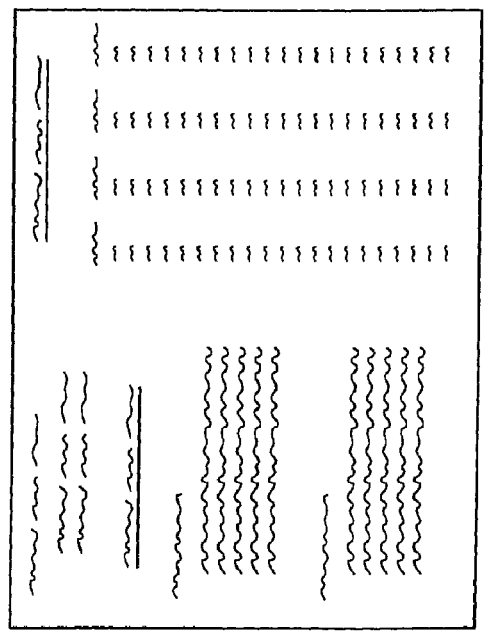
Figure 10:
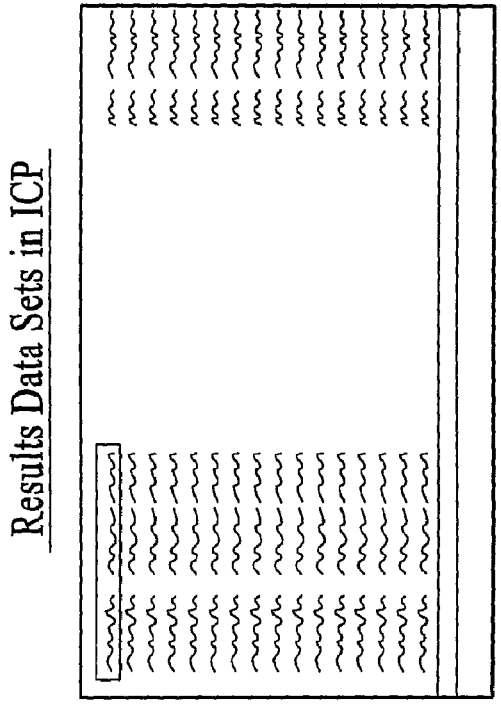
FIG. 10 illustrates the research, development, or engineering experiment workflow previously presented in FIG. 2 adapted to an HPLC method development experiment in which the results are generated by the ICP and automatically imported into the automated experimentation system for automated analysis graphing, and reporting.
Figure 10:
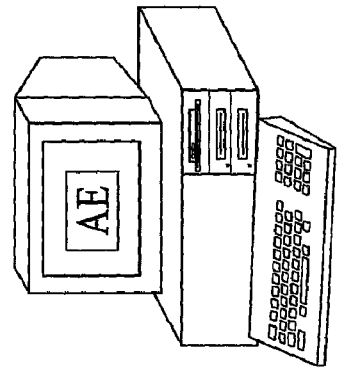

FIG. 9 illustrates the research, development, or engineering experiment workflow previously presented in FIG. 1 adapted to an HPLC method validation experiment created within the AE system's central software environment and automatically transferred to an instrument's ICP. This provides for an automated experiment construction and file-less export to ICP as ready-to-run in the ICP's native data and file formats. FIG. 10 illustrates the research, development, or engineering experiment workflow previously presented in FIG. 1, but again carried out within the AE system's central software environment. This provides for automated experiment running and file-less import from ICP as completed results data sets. The AE system provides an integrated framework to carry out all the required experiment activities without manually transcribing experiments or manually transferring data between environments.

To maintain data exchange security, the AE system in a preferred embodiment contains a complete 21 CFR 11 (Title 21, Part 11, Code of Federal Regulations) Regulatory Compliance feature set that enables maintenance of regulatory compliance across technology platforms. Example regulatory compliance features include:

E-signature controls for data exchanges between instrument platforms.

Full audit trail and event logging for all user/software operations.

Automated e-Review and e-Approvals.

Full audit trail and event logging for all data events and reports.

In addition, the AE system provides a complete workflow management feature set that enables construction of work templates and software-based administration and control of the work. Example workflow management features include:

Ability to create and distribute workflow templates.

Control of feature/function access with user permissions and authorities settings.

Control of workflow with review and approve e-signing control loops.

E-signature control of all data exchanges with ICPs.

Additional Preferred Aspects and Embodiments

In one aspect of the present invention, the HPLC method development experiment is a system comprising one or more of hardware and software components that compute two types of unique surrogate responses, from standard HPLC results data sets, being: Peak Count based responses and Peak Result based responses. Two examples of Peak Count based surrogate responses are Total Peaks and No. of Peaks. As used herein the "Total Peaks" surrogate response operates to automatically determine the total number of peaks in a chromatogram. The Total Peaks number is typically the number of "integrated" peaks obtained from a chromatogram that has been reprocessed based on user set minimum peak height and/or minimum peak area thresholds. As used herein the "No. of Peaks" surrogate response, when linked to an existing result such as peak resolution by an operator such as $\geq$ a value of X, will automatically determine the number of peaks in a chromatogram with resolution $\geq$X. One should realize that multiple responses can be computed at a time for various values of X, the value of X can be made settable by the user and the default X value for HPLC applications is typically but not restrictively set at 1.5. Two examples of Peak Result based operators are Max Peak # and Last Peak. As used herein, when the "Max Peak #" surrogate response is linked to an existing result such as peak resolution and assigned a value of one (1) for #, it will automatically locate the largest peak in a given chromatogram, using peak area as the basis of identifying the largest peak, and automatically retrieve the resolution result for that peak. Likewise, when the "Last Peak" surrogate response is linked to an existing result such as peak resolution, it will automatically locate the last eluting peak in a given chromatogram, and automatically retrieve the resolution result for that peak.

For the present invention, references to these unique surrogate responses are termed "Trend Responses", since these data contain the information on the key trends in chromatographic quality as the experiment variable settings are systematically changed across the experiment trials. For the present invention, since the key trends are in terms of chromatographic characteristics most consequential to the ability to accurately measure compound amount in a sample, the trend responses directly support the standard HPLC method development goals. It should be noted that computing the trend responses defined above for the present invention does not require any assignments of peaks to sample compounds in the chromatogram providing the source data for the computation.

Figure 11:
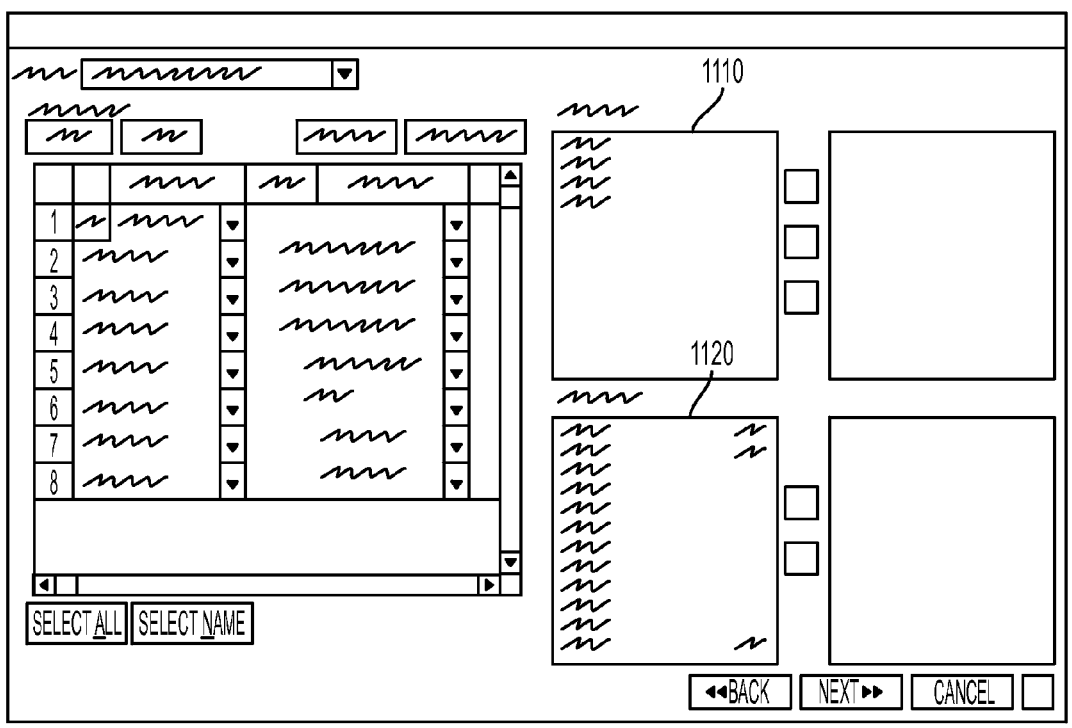
FIG. 11 is an example of a software dialog enabling the user to select one or more operators and value settings which together define the desired surrogate responses to be derived from the experiment results, referred to as Trend Responses in this embodiment and figure.

In a preferred embodiment of the present invention, the invention includes a software solution. FIG. 11 is an example of a software dialog used to input a user settable value of X as the basis of computing the Resolved Peaks trend response.

In FIG. 11 a wizard 1100 dialogue is set forth in which results data from experimentation is sought to be obtained from instrumentation and other devices in communication relation with the wizard 1100. A user using the wizard 1100 imports experimental results data automatically, as instructed via the wizard dialogue, from software and related instrumentation platforms associated with the wizard 1100. The importation of identified data of interest is determined by a user by selectively setting and choosing data gathering characteristics such as compound information 1110, and response data information 1120, for instance but not limitation. Once these results characteristics are defined, the present invention both automatically gathers data and information in relation to the results characteristics sought and is able to automatically adjust settings of connected system instrumentation and software applications for each relevant experimental trial.

In support of the present invention, Fusion AE can automatically compute the trend responses from integrated peak data available in most chromatography data system (CDS) software. In the present invention, Fusion AE can automatically obtain the integrated peak data from the programmatic interface of the CDS. Thereafter, operatively, from analyses of the trend response data sets, the determination and importation of which is also supported by wizard 1100 dialog using for example the response data information and resolution thresholds data, Fusion AE determines the best performing combination of the experiment study factors.

Figure 12:
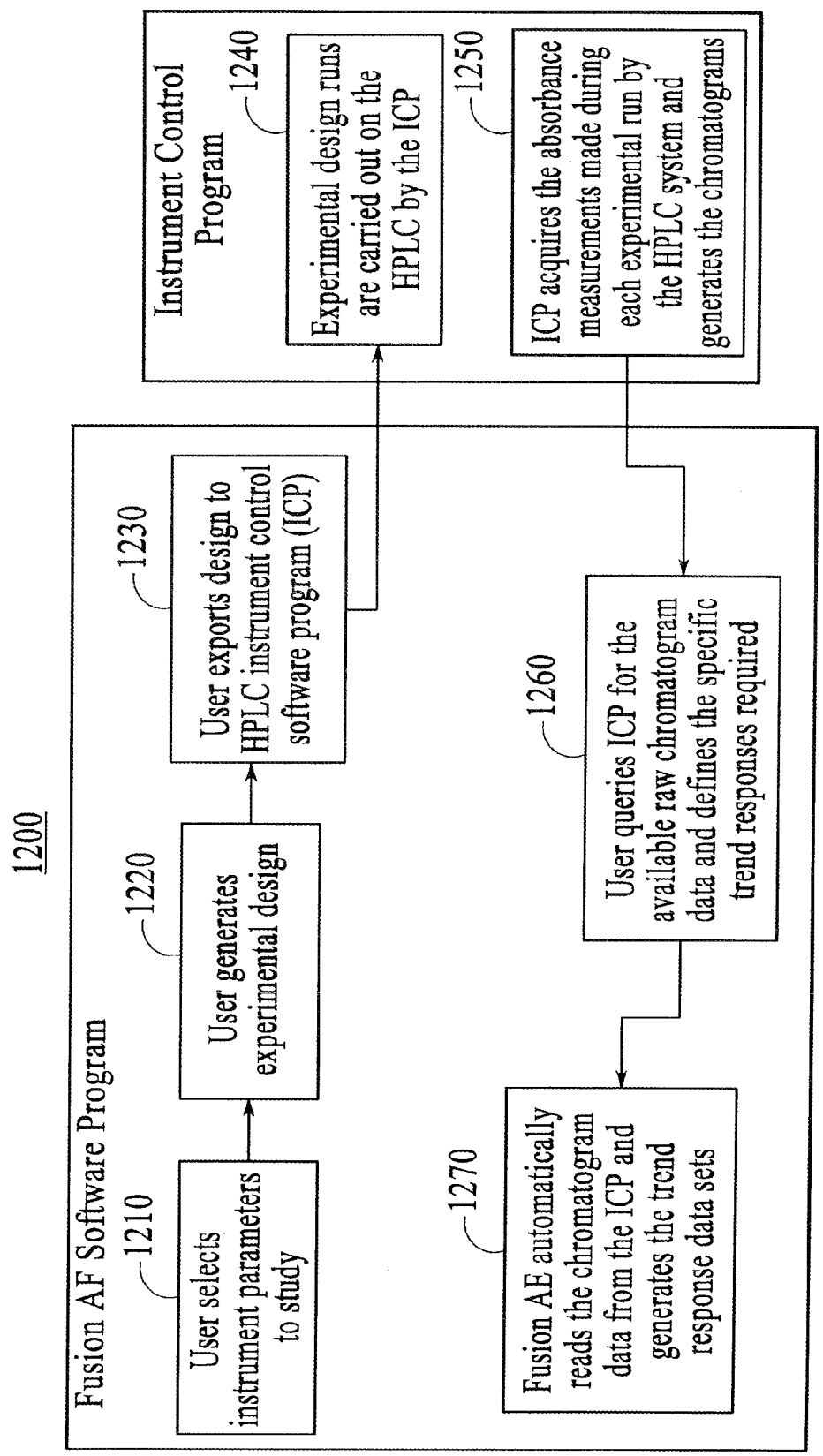
FIG. 12 presents the operational functional flow of the invention in a preferred embodiment including the HPLC method development experiment.

In a preferred embodiment of the present invention, the invention includes a functional flow application, such as that combining hardware and software components in communication like the Fusion AE Software Program and an associated Instrument Control Program of an HPLC System, but not necessarily limited thereto, as depicted in FIG. 12. FIG. 12 presents the operational functional flow 1200 of the invention in a preferred embodiment including the HPLC method development experiment.

In FIG. 12, from the process flow 1200, using the software methodology of the present invention a user selects the instrument parameters to use in the experiment of interest at 1210. Once selected, the user then generates an experimental design in view of the desired experiment and trials sought at 1220. At 1230, the user exports the design to HPLC instrument control program (ICP) in which the HPLC settings are electronically adjusted between trials in response to settings received from the user selected study parameters of 1210.

At 1240, the HPLC instrumentation performs the desired experiments in accordance with the predetermined settings information received from the user via the software instructions. At 1250, the ICP automatically detects and communicates data associated with absorbance measurements made during each experimental run of the HPLC. Additionally and preferably, at 1250, data associated with a chromatogram is also generated automatically in response to the received settings information.

At 1260, the user is able to query the ICP for the available data (i.e., raw chromatogram data) and set via the software the desired trend responses sought. Once acquired, the raw data are automatically converted into chromatogram (i.e., chromatogram) data from the ICP and generates the response data sets at 1270.

As is used herein, the terms "settings," "instrument parameters," "HPLC settings," "predetermined settings," "software instructions," and "data" may include but are not limited to controllable settings and study factor settings as used throughout and herein. Such terms may reference compound choices, selective blends, proportional aspects of select characteristics, feed rates, temperature gradients, and any controllable element of a process step in view of settable characteristics of instrumentation, hardware and/or software associated with the experiment.

As used herein the term "trend responses" is intended to mean information that comprises one or more of the four properties of surrogate responses required to overcome the systemic limitations inherent in HPLC method development experiments described previously, including data content that: (1) is numerically analyzable; (2) is more easily or directly obtained than the current practice results data in which inherent data loss occurs; (3) is usable without the need for associating each peak with a compound (peak tracking) in each of the experiment chromatograms which would otherwise have been required to provide the required data on instrument change effects and which would in many cases not be available due to the inherent data loss associated with peak overlap; (4) provides a response data value for each experiment trial undertaken; and/or (5) provides information on the effects of the changes made to the process or system that would have been obtainable if the experiment samples had no inherent data loss. Further, it is intended definitionally to be that a trend response measures a characteristic of the experimental system that will normally be present and expressed in each experiment trial. For example and not by way of limitation, in HPLC method development, one or more absorbance peaks will normally be present in the chromatogram result obtained for each experiment trial, so there will normally be no inherent missing trend response data. However, under certain operating conditions that may be represented in an experiment trial a chromatogram result may be obtained in which no peaks are present. In this case valid trend response data will still be computed from the chromatogram result.

Exemplary Experimental Trend Response of the Present Invention

FIG. 15 presents examples of Peak Count based Trend Response data computed in an experimental use scenario of the present invention implementing Fusion AE from the HPLC method development experiment discussed previously. It is evident from FIG. 15, that as opposed to the missing impurities resolution data problem associated with the current practice data set, FIG. 15 has a result for each displayed trend response for each run.

FIG. 16 presents the regression analysis results for the Total Peaks trend response. FIG. 16 sets forth two critical results in particular. First, all equation (study parameter effect) terms are statistically significant. This is seen from the significance test values associated with each term in the table (P-Value less than 0.0500, F-Ratio value >4.0000, zero outside the 95% confidence interval). Second, all study parameters are represented in the equation in a form related to the nature of their effects (nonlinear, interaction, etc). From FIG. 16, a ranking of the effect coefficients identifies the largest effect as due to changing columns (Column B in the table represents the effect of switching from Column A to Column B). These results also are demonstrative that a predictive equation was able to be derived from the Total Peaks trend response surrogate data that numerically relates the study parameter effects to one key aspect of compound separation—the visualization of all compounds present in the sample.

FIG. 17 presents the regression analysis results for the Resolved Peaks (>1.50) trend response. As for the Total Peaks response all equation (study parameter effect) terms are statistically significant, and all study parameters are represented in the equation in a form related to the nature of their effects (nonlinear, interaction, etc). These results are also demonstrative that a predictive equation was able to be derived from the Resolved Peaks trend response surrogate data that numerically relates the study parameter effects to a second key aspect of compound separation—the separation of each compound from all other compounds to the extent required.

It should be evident to one of ordinary skill in the art that these two Peak Count based trend responses are complimentary to the key analytical method development goals of visualizing and adequately separating all compound peaks present in the sample, and achieving one goal does not necessarily guarantee that the other goal will also be achieved. For example, the best instrument settings for the Total Peaks response may result in peaks being present for all compounds, but only some compounds being separated to the degree required. Conversely, the best instrument settings for the Resolved Peaks response may resolve almost all compounds but leave two or more peaks completely unresolved.

In the HPLC method development embodiment the Trend Response approach will not necessarily yield the optimum HPLC method (instrument parameter settings) in a single experiment, and indeed in this embodiment it is not meant to. The Trend Response approach of the present invention is a phased approach in which the trend responses enable the experimenter to identify the best settings of parameters such as Column Type and pH; parameters that normally have the greatest effect on separation and therefore cause the most inherent data loss. Once these settings are identified, these parameters are then held constant in a second experiment to optimize the HPLC instrument method.

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. An automated system for reducing inherent data loss associated with experimentation comprising:
    an automated experimentation platform (AEP) for automating one or more experimentation processes;
    a generalized exchange module (GEM) for automating data exchanges between said AEP and one or more target applications and for enabling the data exchanges to be generic with one or more attached components including any of instrumentation, device, software application or ICP; and
    a means for selectively predetermining study factors for said experimentation, wherein one or more unique surrogate response data sets are derived from said experimentation, wherein said one or more unique surrogate response data sets each have primary characteristics that include being numerically analyzable, being readily or directly obtainable when the inherent data loss occurs, being a response value for an experiment trial, and providing information on effects of changes made to said study factors.

2. The system of claim 1, wherein said study factors are inclusive of one or more controllable settings or controllable parameters.

3. The system of claim 2, wherein said controllable settings include one or more of any instrument settings, controllable features of instrumentation, variable characteristics of experimentation, processes of experimentation, or experimental factors in accordance with said experimentation.

4. The system of claim 1, wherein said means is a software application in communication with one or more instruments of said experimentation.

5. The system of claim 1, wherein said system includes a liquid chromatograph (LC), wherein the LC can be one of several types of LC including a high-performance liquid chromatograph (HPLC) or an ultra-high performance liquid chromatograph (UHPLC).

6. The system of claim 2, further comprising a method of computing surrogate responses, wherein said method comprises:
    setting one or more results characteristics in response to said controllable settings;
    obtaining one or more results data sets from a data source of said system; and
    determining unique surrogate responses to include but not be limited to Peak Count based surrogate responses and Peak Result based surrogate responses.

7. The system of claim 6, wherein the Peak Count based surrogate responses include a Total Peaks surrogate response and a Number of Peaks surrogate response, further wherein:
    the Total Peaks surrogate response automatically determines a total number of peaks in a chromatogram, wherein the total number of peaks in the chromatogram is typically the number of "integrated" peaks obtained from a chromatogram that has been reprocessed based on user set minimum peak height and/or minimum peak area thresholds; and
    the Number of Peaks surrogate response, when linked to an existing result such as peak resolution by an operator such as $\geqq$ and a value of X, will automatically determine a number of peaks in a chromatogram with resolution $\geqq X$.

8. The system of claim 7 wherein the Peak Result based surrogate responses include a Max Peak # surrogate response and a Last Peak surrogate response, further wherein:
    the Max Peak # surrogate response links to an existing result such as peak resolution and is assigned a value of one (1) for #, wherein Max Peak "1" automatically locates a largest peak in a given chromatogram using peak area and retrieves a resolution result for the located largest peak; and
    the Last Peak surrogate response links to an existing result such as peak resolution, automatically locates a last eluted peak in a given chromatogram, and retrieves a resolution result for the last eluted peak.

9. The system of claim 8, wherein said method further comprises:
    obtaining multiple surrogate responses using one or more predetermined trend response operators with associated values of X, wherein said value of X may be either a default, predetermined, or user entered value.

10. The system of claim 9, wherein said value of X is determinable by a user through a graphical user interface.

11. The system of claim 9, further comprising a wizard application in which said system is operable in response to selection of one or more controllable parameters of results characteristics determined by a user.

12. The system of claim 7, wherein said surrogate responses are trend responses having chromatographic quality.

13. The system of claim 12, wherein said trend responses are provided in terms of compound separation for improved accuracy in measurement of one or more compound amounts in a sample for said experimentation and are in direct relation to HPLC method development.

14. The system of claim 11, wherein said method further comprises:
    defining one or more settable controllable parameters or results characteristics in a wizard;
    automatically gathering data information in relation to said settable controllable parameters or results characteristics sought; and
    determining automatically an adjustment to controllable settings of said attached components for each relevant experimental trial of said experimentation.

15. The system of claim 14, wherein said method further comprises:
    determining an optimum performing combination of controllable settings or study factors for a next trial of said experimentation.

16. The system of claim 15, wherein said experimentation may include one or more experimentation processes comprising one or any combination of research, development, scientific and engineering processes.

17. The system of claim 16 wherein said experimentation may include one or more experimentation processes for separating one or more compounds or determining the presence or absence of one or more impurities or degradants.

18. The system of claim 17 further comprising a Fusion AE or equivalent component.

* * * * *